(12) United States Patent
Ohashi

(10) Patent No.: US 8,647,575 B2
(45) Date of Patent: Feb. 11, 2014

(54) DEVICE FOR MEASURING BLOOD COMPONENT

(75) Inventor: Hirotaka Ohashi, Chiyoda-ku (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 38 days.

(21) Appl. No.: 13/129,945

(22) PCT Filed: Nov. 19, 2009

(86) PCT No.: PCT/JP2009/069622
§ 371 (c)(1),
(2), (4) Date: May 18, 2011

(87) PCT Pub. No.: WO2010/058815
PCT Pub. Date: May 27, 2010

(65) Prior Publication Data
US 2011/0223078 A1   Sep. 15, 2011

(30) Foreign Application Priority Data

Nov. 21, 2008   (JP) .................................. 2008-297869
Mar. 4, 2009    (JP) .................................. 2009-050494

(51) Int. Cl.
*G01N 15/06*   (2006.01)

(52) U.S. Cl.
USPC ........... 422/68.1; 422/52; 422/73; 422/82.01; 422/82.05; 422/82.06; 422/82.08; 422/82.09; 422/82.11; 422/400; 422/401; 422/420; 422/421; 422/422; 422/423; 422/424; 422/425; 422/426; 422/427; 422/428; 422/429; 422/407; 422/501; 422/502; 422/503; 422/504; 436/164; 436/177; 436/43; 436/63; 435/29; 435/4; 435/7.1; 506/30; 250/214.1; 250/251; 250/576; 530/408; 714/752; 600/573; 600/583; 600/584

(58) Field of Classification Search
USPC ......... 422/52, 73, 82.01, 82.05, 82.08, 82.09, 422/82.11, 99, 102, 407, 501, 502, 503, 422/504, 400, 401, 420, 421, 422, 423, 424, 422/425, 426, 427, 428, 429, 68.1; 436/164, 177, 43, 63, 149, 172, 174, 436/518, 805, 809; 506/30; 435/29, 4, 6, 435/7.1; 250/214.1, 251, 576; 530/408; 714/752

See application file for complete search history.

(56) References Cited

U.S. PATENT DOCUMENTS 5,801,918 A * 9/1998 Ahearn et al. ........... 361/679.55
6,493,069 B1   12/2002 Nagashimada et al.
(Continued)

FOREIGN PATENT DOCUMENTS

JP   11-332378 A   12/1999
JP   2000-046834 A   2/2000
(Continued)

OTHER PUBLICATIONS

International Search Report (PCT/ISA/210) issued on Feb. 9, 2010, by Japanese Patent Office as the International Searching Authority for International Application No. PCT/JP2009/069622.

(Continued)

*Primary Examiner* — Dennis M White
(74) *Attorney, Agent, or Firm* — Buchanan Ingersoll & Rooney PC

(57) ABSTRACT

A blood glucose meter includes a front attachment part to which a test piece is attached, a measurement part for measuring a component of blood collected via a blood guide passage in the test piece, and a monitor for displaying the measurement results obtained by the measurement part. When the device is placed on a horizontal plane by referring to the display face of the monitor as the upper side and the opposite side as the lower side and placing the display face of the monitor upward, the central axis of the test piece extends obliquely downward toward the front side. The blood glucose meter comprises a main part provided with the monitor and a linking part between the main part and the front attachment part. The top face of the linking part is placed roughly parallel to the central axis line and is provided with an ejector lever.

17 Claims, 22 Drawing Sheets

(56) References Cited

U.S. PATENT DOCUMENTS

| | | |
|---|---|---|
| 7,077,328 B2 | 7/2006 | Krishnaswamy et al. |
| 2002/0060247 A1* | 5/2002 | Krishnaswamy et al. ............... 235/472.01 |
| 2004/0138588 A1* | 7/2004 | Saikley et al. ............... 600/583 |
| 2006/0078658 A1* | 4/2006 | Owens et al. ............... 426/231 |
| 2007/0233395 A1 | 10/2007 | Neel et al. |
| 2009/0099864 A1 | 4/2009 | Cronrath et al. |
| 2010/0069792 A1 | 3/2010 | Fujimura et al. |
| 2010/0317092 A1 | 12/2010 | Suzuki et al. |

FOREIGN PATENT DOCUMENTS

| | | |
|---|---|---|
| JP | 2001-021556 A | 1/2001 |
| JP | 2006-517651 A | 7/2006 |
| JP | 2007-054407 A | 3/2007 |
| JP | 2007-068839 A | 3/2007 |
| JP | 3135393 u | 9/2007 |
| JP | 2008-200438 A | 9/2008 |
| JP | 2008-535599 A | 9/2008 |
| JP | 3155842 U | 12/2009 |
| WO | WO 2007/118046 A2 | 10/2007 |
| WO | WO 2008/087876 A1 | 7/2008 |
| WO | WO2009/099148 A1 | 8/2009 |

OTHER PUBLICATIONS

Written Opinion (PCT/ISA/237) issued on Feb. 9, 2010, by Japanese Patent Office as the International Searching Authority for International Application No. PCT/JP2009/069622.

* cited by examiner

DEVICE FOR MEASURING BLOOD COMPONENT

TECHNICAL FIELD

This invention relates to a blood component measuring apparatus (device) for measuring a component such as glucose from blood sampled through a blood introduction path in a test piece, which is mounted on a distal end mounting portion of the blood component measuring apparatus.

BACKGROUND ART

Daily management by measurement of variations in blood glucose levels is recommended to diabetics. A blood glucose meter has been placed into practical use, in which a measurement portion, such as a test paper impregnated with a reagent that develops a color in response to the amount of glucose in blood, is provided. Blood is applied to the test paper so that the test paper develops a color, and the degree of the color is measured optically and calculated in order to display the blood glucose level (for example, refer to Japanese Utility Model Registration No. 3135393 (FIGS. 2 and 8), Japanese Laid-Open Patent Publication No. 2000-046834, and U.S. Pat. No. 7,077,328). The test paper is provided on a disposable test piece, and the test piece is mounted on a distal end mounting portion of the blood glucose meter. Further, a blood glucose meter in which an electric chemical sensor is used has also been placed into practical use.

When blood of a diabetic is to be sampled, the skin (for example, a finger, a palm, or the like) is punctured first by a predetermined puncture device, and blood is debouched by a small amount after the puncture. Then, a test piece is mounted on the blood glucose meter and a spotted portion at the distal end of the test piece is brought into contact with a blood drop, whereby the blood is introduced to the test paper by capillary action through a communication path having a very small diameter.

On the other hand, blood glucose meters in recent years are demanded not only for personal use, in which a diabetic uses the blood glucose meter to measure the blood glucose levels daily, but also for hospital use, in which a health care worker carries out measurement with regard to plural patients who are hospitalized in medical facilities.

Incidentally, many diabetics are elderly and sometimes use of fingers or hands in such diabetics is made troublesome due to complications from diabetes. Further, even if able to freely use the fingers or hands, some patients may not be able to handle a blood glucose meter well due to shaking of the fingertips due to psychological factors or the like, if the patient is unaccustomed to operation of the blood glucose meter. In particular, since a blood drop obtained by puncturing is very small, it is not always easy for a diabetic to place the spotted portion of the test piece into contact with the blood drop. Further, if the procedure described above is carried out with trembling hands, sufficient blood may not be impregnated into the test paper, even if the spotted portion comes into contact with the blood drop. In such a case, since a correct measurement result of the blood glucose level is not obtained, puncturing must be carried out again to attempt measurement after the test piece has been exchanged.

According to research carried out by the inventor of the present application, it has been found that there are many patients whose hands are unstable if both arms are left in a free state in the air, thus making it difficult to bring the spotted portion into contact with the blood drop. However, the hands can be stabilized if the patient's wrist or peripheral portions of the wrist are placed on a table.

However, many patients have been found who fail, if their wrists are placed on a table, to suitably set the direction of the blood glucose meter, due to the fact that the degree of freedom in operation of the wrists is suppressed, and ultimately it is difficult to bring the spotted portion into contact with the blood drop. In particular, as seen in FIG. 21, while a blood drop 900 obtained by puncture is positioned in a substantially upward direction on one of the hands (hereinafter referred to as the left hand) so that the blood drop 900 cannot fall off, a blood glucose meter 901 and a test piece 902, which are grasped by the right hand, are directed obliquely upwardly (refer to the arrow in FIG. 21), and therefore it is difficult to bring the spotted portion 903 at the distal end into contact with the blood drop 900.

Further, as seen in FIG. 22, where a spotting operation is carried out in midair, if the blood drop 900 is directed substantially upward, then the blood glucose meter 901 approaches the blood drop 900 from an upward or obliquely upward location. Therefore, the blood drop 900 or the spotted portion 903 of the test piece 902 is placed in a blind spot by the blood glucose meter 901 and the right hand. Such a situation impairs visibility and sometimes makes it less easy to carry out the spotting operation. Since the spotted portion of the test piece is an operation carried out upon measurement of blood glucose levels, good visibility upon operation is demanded. Also, even when the blood glucose meter is placed on a table, visibility still is demanded to enable confirmation of the state of operation.

Further, even with a health care worker who is skilled in operating the blood glucose meter, to bring the spotted portion into contact with the very small blood drop requires attentiveness. In particular, where measurements are carried out for a great number of patients, it is desirable to carry out the measurement process for all individuals as easily and conveniently as possible, and thus it is desirable to secure visibility of the spotted portion.

Further, it is desirable to prevent application of unnecessary external forces to the test piece that is mounted on the blood glucose meter when the blood glucose meter is placed on a table.

Further, when the blood glucose meter is placed on a table, it is desirable for the test piece to be spotted on the blood after the spotted portion has been positioned in advance with respect to proximity of the blood drop.

Further, since multiple patients and a plurality of health care workers (nurses, doctors, and so forth) exist within medical facilities, in a case where the blood glucose meter is intended for hospital use, specifications different from those for personal use are required.

In particular, while some blood glucose meters have a function for storing measurement values of blood glucose levels carried out a plural number of times, since it is supposed that one blood glucose meter is used for measurement of blood glucose levels of multiple patients in a medical facility, there is the necessity to store measured blood glucose levels in a state in which the blood glucose levels are distinguishable for individual patients. Further, for recording and traceability, it is desirable to make it possible to specify an operator who carries out measurement of blood glucose levels at each time of measurement. In order to specify a patient and an operator in the foregoing manner, it is necessary to read identification information of the patient and the operator into the blood glucose meter.

Furthermore, it is desirable for acquisition of such identification information to be carried out quickly and stably without causing discomfort to the patient.

On the other hand, the blood glucose meter disclosed in U.S. Pat. No. 7,077,328 described above also has several problems.

First, since a barcode reader is provided at the distal end, there is a possibility that a laser beam emitted upon scanning may be directed toward the patient and cause the patient to experience discomfort.

Secondly, since the barcode reader and a distal end measurement portion are disposed very near to each other, there is a possibility that a test piece, which is mounted on the distal end measurement portion, may hit against some different body (including a living body) upon reading of the barcode. If such a hit occurs before measurement of the blood glucose level is taken, then there is a possibility that the spotted portion of the test piece may become soiled or broken, resulting in a measurement failure. Further, if such a hit occurs after measurement of the blood glucose level, since blood sticks onto the spotted portion, a different body with which the spotted portion comes into contact may become soiled.

Thirdly, since a monitor is disposed in proximity to the distal end measuring portion, the distal end portion has a considerable size, which impedes balance. Further, since a gripping portion is positioned rearwardly with respect to the monitor, the gripping portion is positioned far from the distal end measuring portion. As a result, the distal end measuring portion is likely to become unstable.

SUMMARY OF INVENTION

The present invention has been made taking the above matters into consideration. A first object of the present invention is to provide a blood component measuring apparatus, which allows a spotted portion of a test piece to be brought into contact readily and with certainty with a blood drop obtained by puncture, thereby to suppress errors in measurement. A second object of the present invention is to provide a blood component measuring apparatus, which can carry out reading of data simply, conveniently, quickly and stably.

According to the present invention, a blood component measuring apparatus is provided on which a test piece is mounted, including a distal end mounting portion on which the test piece is capable of being mounted, a measuring portion adapted to measure components of blood sampled through a blood introduction path provided in the test piece that is mounted on the distal end mounting portion, and a monitor adapted to display a result determined by the measuring portion and a predetermined control section, wherein a display face of the monitor is defined as an upper side, while an opposite face to the display face is defined as a lower side, and wherein, when the blood component measuring apparatus is placed on a horizontal plane in a state in which the display face of the monitor is directed upwardly, a center axial line of the test piece is directed obliquely downward toward the distal end side.

By shaping the blood component measuring apparatus in this manner, such that, when the blood component measuring apparatus is placed on a horizontal plane, the center axial line of the test piece is directed obliquely downward toward the distal end side, it becomes easy to orient the spotted portion of the test piece in a direction toward the blood drop. Consequently, the spotted portion of the test piece can be brought into contact readily and reliably with a blood drop obtained by puncture, whereby measurement errors can be suppressed.

Further, according to another aspect of the present invention, a blood component measuring apparatus according to the present invention is provided on which a test piece is mounted, including a distal end mounting portion on which the test piece is capable of being mounted, a measuring portion adapted to measure components of blood sampled through a blood introduction path provided in the test piece that is mounted on the distal end mounting portion, and a monitor adapted to display a result determined by the measuring portion and a predetermined control section, wherein a display face of the monitor is defined as an upper side, while an opposite face to the display face is defined as a lower side, and wherein a center axial line of the test piece is directed, as viewed in side elevation, obliquely downward toward the distal end side with reference to a line of extension of the display face of the monitor.

By shaping the blood component measuring apparatus in this manner, such that the center axial line of the test piece is directed obliquely downward toward the distal end side with reference to the line of extension of the display face of the monitor, it becomes easy to direct the spotted portion of the test piece in a direction toward the blood drop. Consequently, the spotted portion of the test piece can be brought into contact readily and reliably with a blood drop obtained by puncture, whereby measurement errors can be suppressed.

An angle defined by the line of extension and the center axial line may be 10° to 40°. According to such an angle setting, the spotted portion of the test piece is oriented more correctly in a direction toward the blood drop.

The blood component measuring apparatus may further include a main portion on which the monitor is provided, and an intermediate portion provided between the main portion and the distal end mounting portion, wherein an upper face of the intermediate portion is set substantially parallel to the center axial line. On such an intermediate portion, a space in which several mechanisms relating to the distal end mounting portion can be provided is assured in a preferred direction. Further, since the intermediate portion is provided, it is easy to direct the center axial line of the test piece obliquely downward toward the distal end side. Moreover, by setting the upper face of the intermediate portion substantially parallel to the center axial line of the test piece, it is easy to visually grasp the direction of the test piece.

An ejector lever for removing the mounted test piece by performing a push out operation toward the distal end side may be provided on the upper face of the intermediate portion. By this configuration, the ejector lever moves along the upper face and can be operated readily. Further, a space for movement of the ejector lever can be assured.

As viewed from above, the intermediate portion may have a width that decreases continuously and concavely from the main portion toward the distal end side. By this configuration, the intermediate portion is made suitably thin and further has a concave shape. Consequently, the intermediate portion can be grasped readily by the fingers. Further, since the intermediate portion is positioned near to the distal end mounting portion, by grasping the intermediate portion, the test piece that is mounted thereon can be stabilized.

A thickness of the main portion in a vertical direction may be substantially fixed, and as viewed in side elevation, the main portion and the intermediate portion may be connected to each other by a continuously curved face portion, the lower face of which has a concave shape. It is easy to place a finger on such a concave and continuous curved face, and thus it is easy to grasp the blood component measuring apparatus.

The blood component measuring apparatus may be configured such that, when the test piece is mounted on the distal end mounting portion and the blood component measuring apparatus is placed on the horizontal plane, in a state in which the display face of the monitor is directed upwardly, a distance between a spotted portion at the distal end of the test piece and the horizontal plane is 3 mm to 30 mm. By this configuration, it is possible to place a finger or a hand, on which a blood drop has been formed, on a table, and in a state in which the finger or hand remains placed on the table, the blood glucose meter can be moved toward the blood drop to perform blood spotting. Therefore, even a patient whose fingers are impaired can readily perform blood glucose measurement. Further, when the blood component measuring apparatus is left placed on the table, visibility of the spotted portion is good and the state of the spotted portion can be confirmed.

When the blood component measuring apparatus is placed on the horizontal plane in a state in which the display face of the monitor is directed upwardly, the distance between a highest point of the lower face and the horizontal plane may be 3 mm to 20 mm. By this configuration, when the blood component measuring apparatus is placed on a table, a suitable gap is assured for enabling placement of the fingers.

When the test piece is mounted on the distal end mounting portion and the blood component measuring apparatus is placed on the horizontal plane in a state in which the display face of the monitor is directed upwardly, the test piece may be spaced away from the horizontal plane. By this configuration, unnecessary external forces are prevented from being applied to the test piece.

The blood component measuring apparatus according to the present invention is shaped such that, when the blood component measuring apparatus is placed on a horizontal plane, the center axial line of the test piece is directed obliquely downward toward the distal end side. (In other words, the blood component measuring apparatus is shaped such that the center axial line is directed obliquely downward toward the distal end side, with reference to a line of extension of the display face of the monitor.) Consequently, it is easy to direct the spotting portion of the test piece in a direction toward the blood drop, and it is possible to place the spotted portion of the test piece into contact with the blood drop, which is obtained by puncture, readily and reliably. Thus, measurement errors can be suppressed.

According to another aspect of the present invention, a blood component measuring apparatus is provided on which a test piece is mounted, including a distal end mounting portion on which a test piece is capable of being mounted, a measuring portion adapted to measure components of blood sampled through a blood introduction path provided in the test piece that is mounted on the distal end mounting portion, and a monitor adapted to display a result determined by the measuring portion and a predetermined control section, optical data reading means provided at a rear end, a main portion on which the monitor is provided, an intermediate portion provided between the main portion and the distal end mounting portion, and a curved face portion, which serves as a connection portion between the main portion and the intermediate portion, and the lower face of which has a concave shape as viewed in side elevation.

Since the optical data reading means is provided at the rear end portion, the optical data reading means is spaced away from the distal end mounting portion and is directed in an opposite direction. Consequently, upon reading of data, the test piece can be prevented from hitting against a different body. Further, the concave curved face portion can be used as a grasping portion, and the concave curved face is positioned near the distal end mounting portion. Therefore, it is easy to adjust the location of the spotted portion of the test piece with respect to the blood drop, and thus a stabilized operation can be achieved. In this manner, with the blood component measuring apparatus according to the present invention, reading of data can be carried out simply, conveniently, quickly and stably.

An operation switch for the optical data reading means may be provided on a face on which the monitor is disposed between the monitor and the distal end mounting section.

The location between the monitor and the distal end mounting portion is a position at which it is easy to operate the operation switch, and thus it is preferable to provide the operation switch at such a position. Further, since the operation switch is located at this position, there is no need to change the grasping position of the hand upon measurement of the blood component and upon reading of data, which is efficient. The operation switch is positioned substantially on an opposite side to the curved face portion, and is held by and between a finger (for example, the forefinger), which is placed on the curved face portion, and another finger (for example, the thumb) that presses the operation switch, thereby permitting stabilized grasping and operation.

The optical data reading means may comprise a barcode reader.

The optical data reading means may comprise a camera for reading a two-dimensional code.

As viewed from above, the intermediate portion may have a width that decreases continuously and concavely from the main portion toward the distal end side. By this configuration, the intermediate portion is made suitably thin and has a concave shape. Consequently, the intermediate portion can be grasped readily by the fingers. Further, since the intermediate portion is positioned near to the distal end mounting portion, by grasping the intermediate portion, it is easy to bring the blood drop into contact with the spotted portion of the mounted test piece, so that a stabilized operation can be carried out.

If the radius of curvature of the curved face portion is 5 mm to 25 mm, then the finger can be placed more readily on the curved face portion.

A display face of the monitor may be defined as an upper side, while an opposite face to the display face may be defined as a lower side. Further, as viewed in side elevation, a center axial line of the test piece may be directed obliquely downward toward the distal end side with reference to a line of extension of the display face of the monitor. By shaping the blood component measuring apparatus in this manner, such that the center axial line of the test piece is directed obliquely downward toward the distal end side with reference to the line of extension of the display face of the monitor, it becomes easy to orient the spotted portion of the test piece in a direction toward the blood drop. Consequently, the spotted portion of the test piece can be brought into contact readily and reliably with the blood drop obtained by puncture, and measurement errors can be suppressed.

With the blood component measuring apparatus according to the present invention, simple and convenient data reading can be achieved in a contactless manner. Further, a connector connecting operation, etc., are made unnecessary, and reading of data can be carried out rapidly.

Since the optical data reading means is provided at the rear end portion, the optical data reading means is oriented in a direction opposite to the test piece and the measuring portion at the distal end, and in a direction opposite from the patient. Consequently, the optical data reading means does not cause the patient to experience any discomfort.

Since the curved face portion, the lower face of which is concave, is provided at the connecting portion between the main portion and the intermediate portion, a finger can be placed thereon to stabilize the blood component measuring apparatus. Accordingly, optical reading by the optical data reading means can be carried out in a stable manner.

DESCRIPTION OF EMBODIMENTS

In the following descriptions, an embodiment of a blood component measuring instrument according to the present invention will be described with reference to FIGS. 1 to 20 of the accompanying drawings.

As shown in FIGS. 1, 2, 3 and 4, the blood glucose meter (blood component measuring instrument) 10a according to the present embodiment includes a distal end on which a test piece 12 is mounted. The blood glucose meter 10a has a function of storing values obtained by blood glucose measurements carried out a plural number of times. In medical facilities, the single blood glucose meter 10a can be used for blood glucose measurements of a plurality of patients. First, the test piece 12 shall be described.

Figure 5:
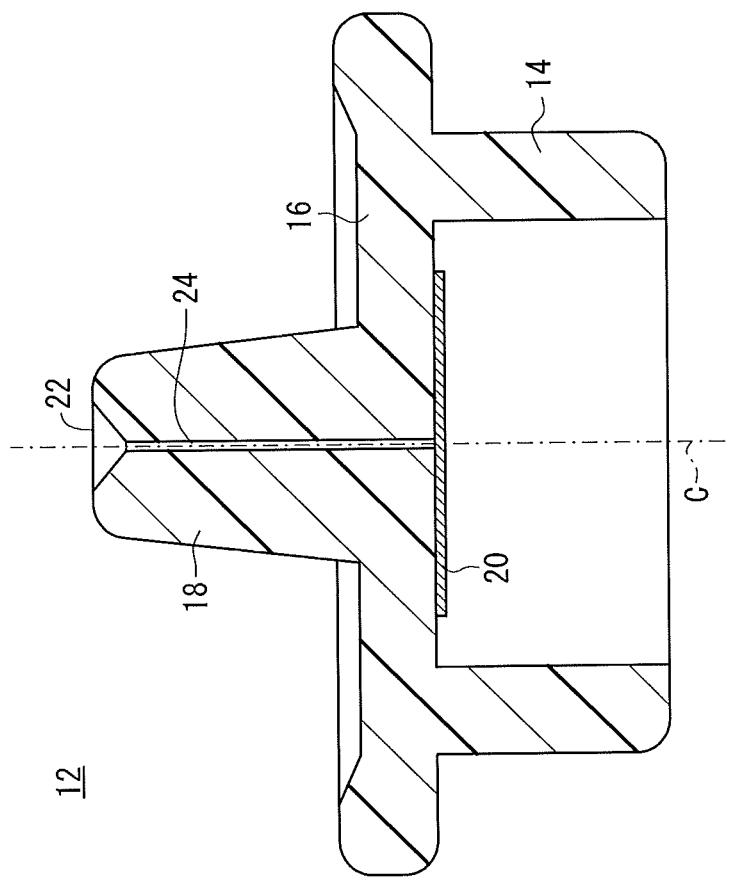
FIG. 5 is a cross sectional view of a test piece.

As shown in FIG. 5, the test piece 12 includes a base tube 14, a flange 16 that covers one end of the base tube 14, a conical projection 18 projecting from the flange 16, and a test paper 20, which is stuck to the rear face of the flange 16. A plurality of slits 14a (refer to FIG. 1) are provided in the base tube 14. A linear blood introduction path 24, which extends from a spotted portion 22 at the end of the projection 18 and which communicates with the test paper 20, is provided at the center of the projection 18. As materials for the test paper 20, for example, polyether sulfone can be used. As a reagent, which is impregnated in the test paper 20, a chromogenic agent such as, for example, glucose oxidase (GOD), peroxidase (POD), 4-aminoantipyrine or N-ethyl-N(2-hydroxy-3-sulfopropyl) can be used. Further, the reagent may contain a predetermined buffering agent. The blood introduction path 24 generally is provided on a center axial line C of the test piece 12. The center axial line C of the test piece 12 forms a straight line that extends in a direction in which the spotted portion 22 of the test piece 12 is directed, the straight line passing through the distal end of the spotted portion 22.

The test piece 12 is a so-called disposable article, and is packaged in an individual package body (not shown) and sterilized in advance. The blood introduction path 24 is set sufficiently small in diameter, to such a degree that the blood introduction path 24 is capable of sucking blood by capillary action, and of introducing the blood, which is brought into contact with the spotted portion 22, to the test paper 20. A conventional article can be applied as is to the test piece 12.

Referring back to FIGS. 1 to 4, the blood glucose meter 10a according to the present embodiment includes a distal end mounting portion 30 on which the test piece 12 is mounted, a measuring portion 32 for measuring a developed color of the test paper 20 caused by a blood component that is sampled through the blood introduction path 24 of the test piece 12, which is mounted on the distal end mounting portion 30, a liquid crystal monitor 34 for displaying a result of measurement by the measuring portion 32 through a control section (microcomputer, etc.) 33, an ejector lever 36 for removing the mounted test piece 12 by carrying out a push out operation toward the distal end side, an operation button group 38, a data reading button 40, and a cap 39 for protecting the distal end mounting portion 30. The blood glucose meter 10a has a smooth shape, which generally is free of angled portions. In order to avoid complexity in illustration, the cap 39 has been omitted from the figures, except FIG. 1. For the measuring portion 32, various mechanisms can be adopted in accordance with the component detection method of the test piece 12.

The blood glucose meter 10a is for hospital use, wherein a hospital care worker uses the blood glucose meter 10a to carry out measurements with regard to plural patients who are hospitalized in a hospital facility. The blood glucose meter 10a includes data recording and calling functions for each patient along with buttons for such functions. The blood glucose meter 10a has a size that is somewhat greater than that of a blood glucose meter 10c for personal use (refer to FIG. 18), which shall be described later. Naturally, the blood glucose meter 10a can also be used as is, as an apparatus for personal use, without applying special remodeling to the blood glucose meter 10a.

The distal end mounting portion 30 has a cylindrical shape to facilitate mounting of the test piece 12. The test piece 12 can be mounted readily and stably on the distal end mounting portion 30 by insertion of the base tube 14 (refer to FIG. 5).

The blood glucose meter 10a is controlled by the internal control section 33 to continuously carry out projection of light to and reception of light from the test paper 20 by means of the measuring portion 32, which is configured from an optical means. Further, the blood glucose meter 10a calculates a blood glucose level by performing a predetermined calculation based on a color reaction of light, and displays the blood glucose level on the monitor 34. If a color reaction of the test paper 20 cannot be observed or is otherwise insufficient, then a predetermined error is displayed. The control procedure for blood glucose level measurement by the blood glucose meter 10a basically is the same as that of a conventional blood glucose meter according to the conventional art.

The monitor 34 includes a blood glucose level display portion 34a for displaying a blood glucose level, and an auxiliary display portion 34b for displaying time and other information. The blood glucose level display portion 34a can display a three digit numerical value and a predetermined character display (for example, characters such as "OK"). Since some diabetics have weak sight, the monitor 34 is set sufficiently large taking visibility into consideration. On the auxiliary display portion 34b, patient identification data, operator identification data, and test piece identification data read by a later described barcode reader 48 also are displayed. The monitor 34 is flat on at least the liquid crystal display face portion thereof.

The operation button group 38 is provided collectively on the proximal end side, and includes a power supply button 38a, movement buttons 38b and 38c, selection buttons 38d and 38e, and an LED display portion 38f. The movement buttons 38b and 38c function to move an item displayed on the monitor 34, or to scroll the screen image together with movement of the displayed item, etc. The selection buttons 38d and 38e operate to select a function, which is displayed on the monitor 34, corresponding to the position thereof. The LED display portion 38f functions to notify a state of the blood glucose meter by means of an LED, which emits light or blinks in various colors.

The ejector lever 36 is a round-shaped lever, which is provided on an upper face 46a in proximity to the distal end mounting portion 30. The ejector lever 36 can suitably be grasped by a finger, and includes a flat portion 36a on the proximal end side and a projecting portion 36b on the distal end side thereof. The ejector lever 36 is movable along the upper face 46a. A plurality of ribs, which extend in a lateral direction, are provided on the flat portion 36a for preventing slippage. The projecting portion 36b has a width and height suitable for being grasped by a finger. The ejector lever 36 is elastically biased toward the proximal end side by means of a suitably weak resilient member. If the ejector lever 36 is grasped by the finger in order to carry out a push out operation toward the distal end side, then the ejector lever 36 moves in parallel to an axial direction of the cylindrically shaped distal end mounting portion 30. Thereupon, the ejector mechanism inside the ejector lever 36 moves in an interlocking relation, so as to push out the test piece 12 and enable removal of the test piece 12 from the distal end mounting portion 30. Further, with the aforementioned configuration, wiping and cleaning in the vicinity of the ejector lever 36 can easily be carried out.

The data reading button 40 is an operation switch for a barcode reader (optical data reading means) 48 provided at a rear end portion. The data reading button 40 can be easily operated if the data reading button 40 is disposed between the monitor 34 and the distal end mounting portion 30 on a face (hereinafter referred to as a monitor face) on which the monitor 34 is provided. Further, since the data reading button 40 is provided at this position, it is unnecessary to change the grasping position of the hand when measurement of a blood component and reading of data are carried out, which is efficient.

A plurality of data reading buttons 40 may be provided at neighboring positions in accordance with applications to be performed thereby (for example, for reading patient identification data, measuring person identification data, and test piece identification data). Further, different processes can be executed in response to operation methods (depending upon a difference in a switch-on time, or a difference in the number of times that switching is performed within a predetermined short time period).

Figure 4:
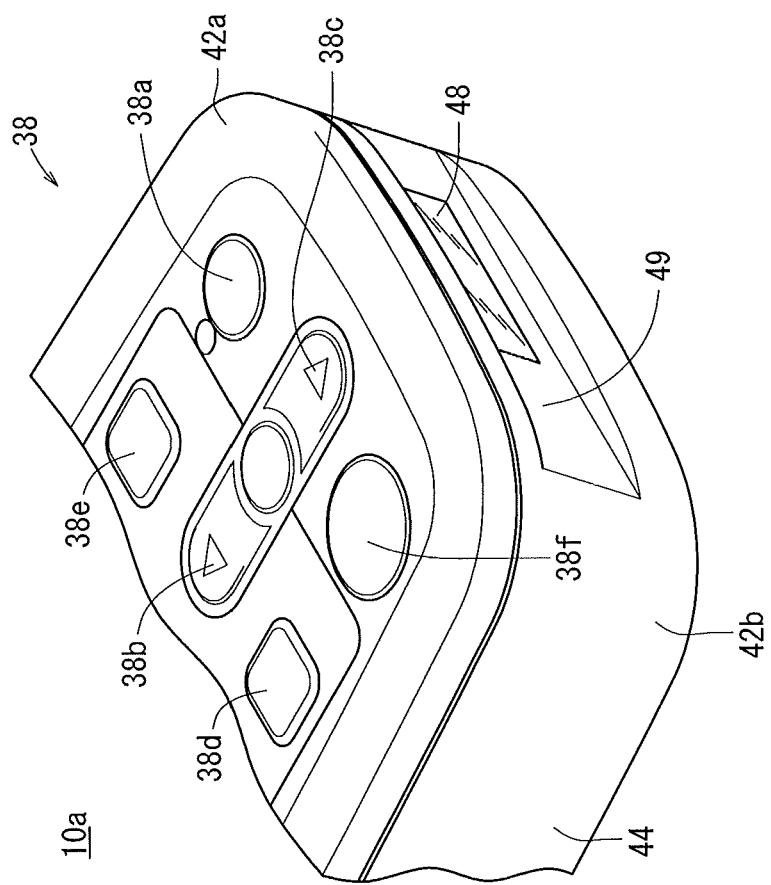
FIG. 4 is an enlarged perspective view of a rear end portion of the blood glucose meter according to the present embodiment.

As shown in FIG. 4, a barcode reader 48 is provided at a concave portion 49 on a rear end portion of the blood glucose meter 10a. The barcode reader 48 serves as a means for reading a barcode in order to obtain patient identification data, measuring person identification data, and test piece identification data by means of laser scanning. The barcode reader 48 is of a conventional laser type and is inexpensive.

Figure 1:
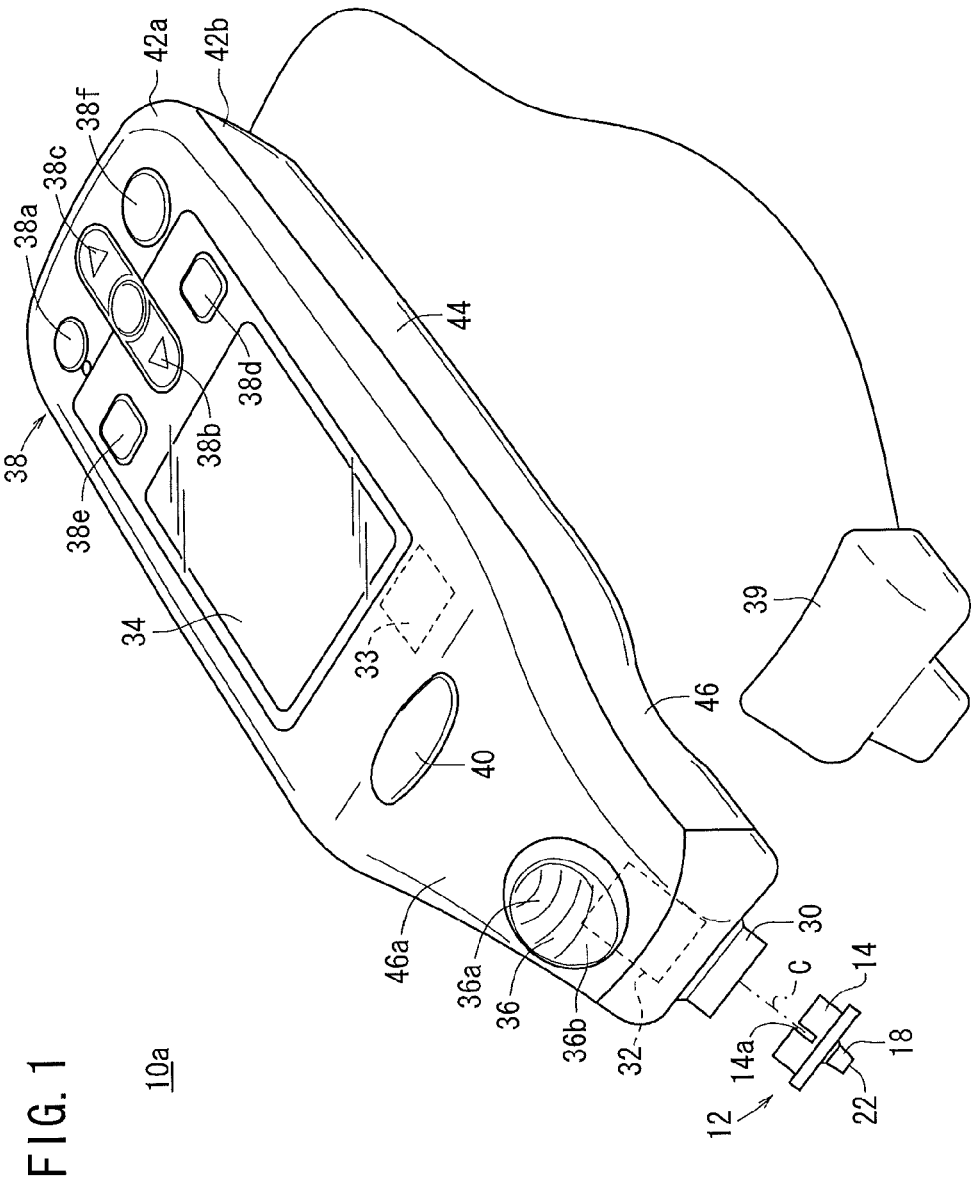
FIG. 1 is a perspective view of a blood glucose meter according to a present embodiment.
Figure 2:
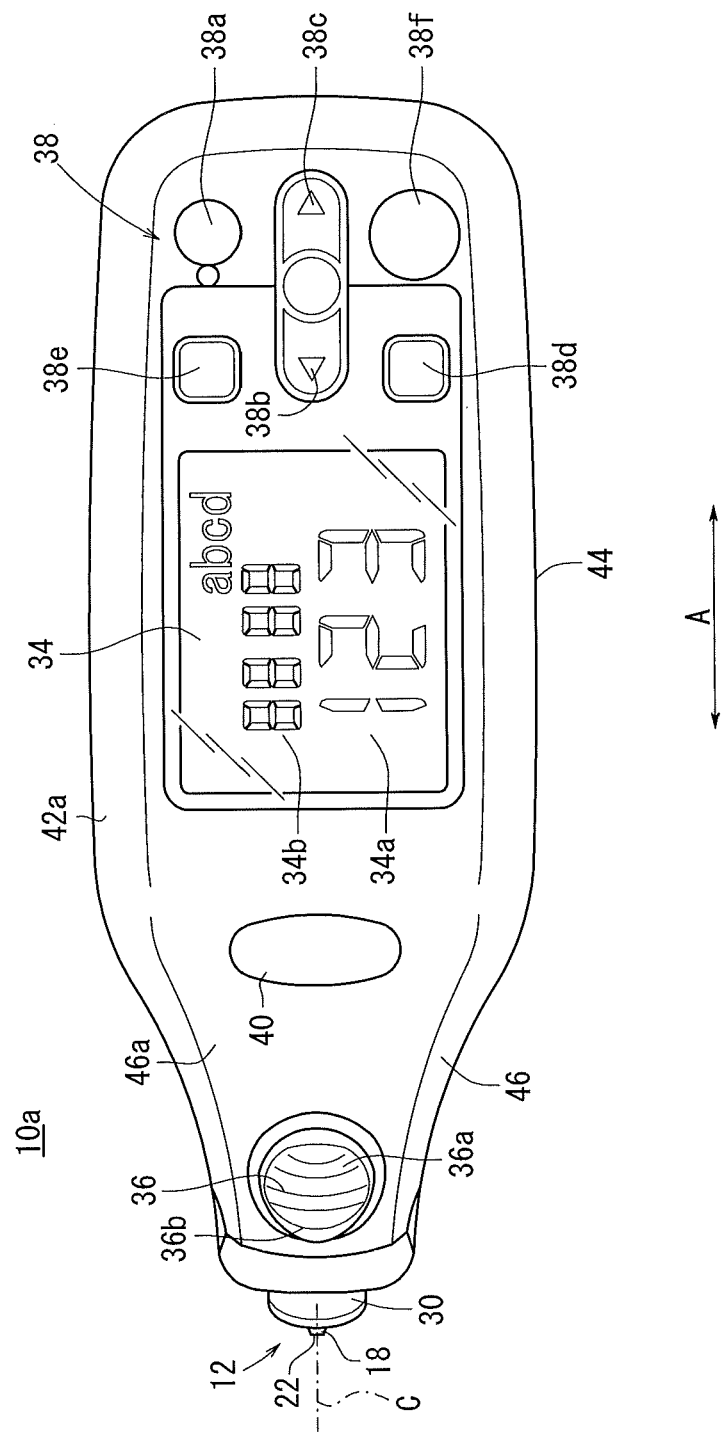
FIG. 2 is a plan view of the blood glucose meter according to the present embodiment.
Figure 3:
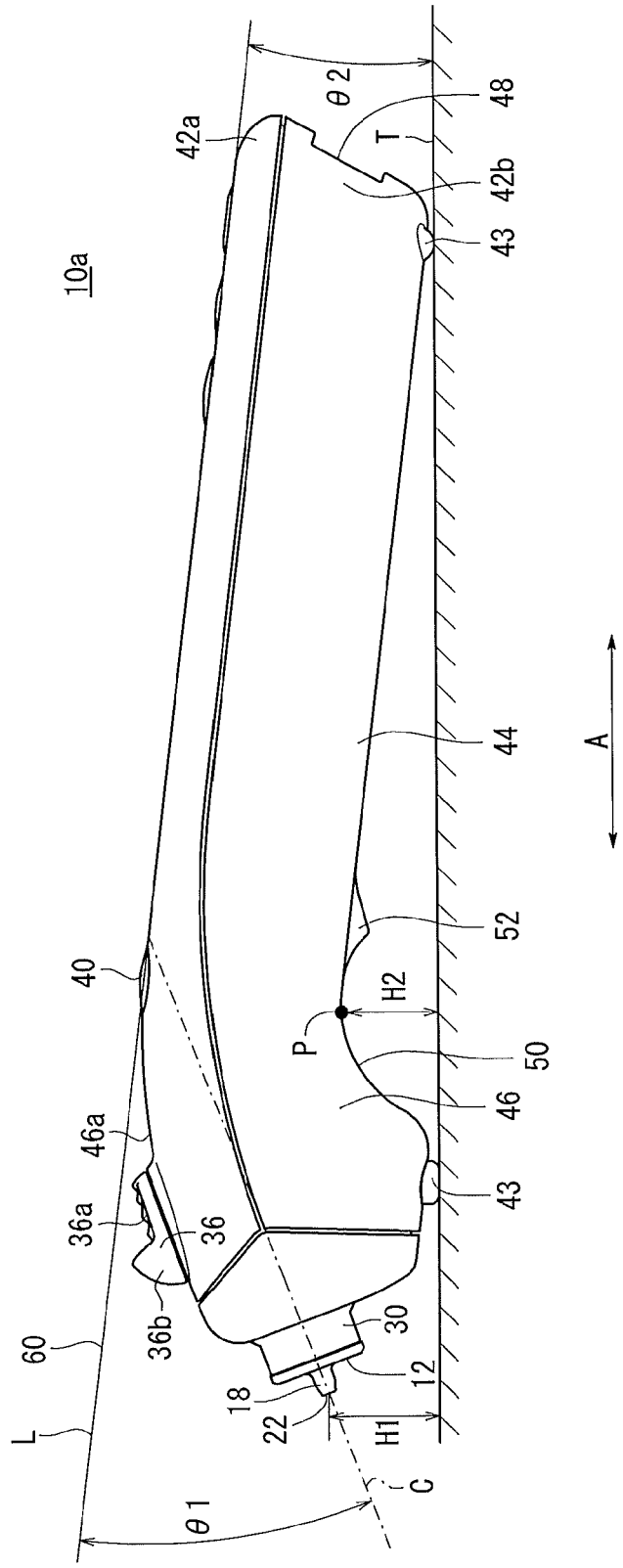
FIG. 3 is a side elevational view of the blood glucose meter according to the present embodiment.

A rear end portion of the blood glucose meter 10a is inclined so as to expand toward the monitor screen as viewed in side elevation (refer to FIG. 3). Since the barcode reader 48 is provided at the aforementioned inclined rear end portion within the concave portion 49, the barcode reader 48 cannot be touched inadvertently, and thus the measurement face is less likely to become soiled.

The blood glucose meter 10a has a function for storing blood glucose measurement values, which are measured a plural number of times, and can store blood glucose measurement values distinctively for individual patients, based on patient identification data read by the barcode reader 48. Further, for so-called traceability, an operator who carries out blood glucose measurements can be specified for each measurement, based on measuring person identification data read by the barcode reader 48. Further, based on identification data for specifying the type of test piece 12, it can be confirmed that an appropriate test piece 12 has been used. Information read by the barcode reader 48 is identified by an operation method of the data reading button 40, and such information is displayed distinctively on the monitor 34. After the patient identification data, the measuring person identification data, and the test piece identification data have been read by the barcode reader 48, a predetermined measurement mode is entered. Consequently, measurements can be started in accordance with the correct procedure.

Since the barcode reader 48 is disposed at the rear end portion, the barcode reader 48 is oriented in an opposite direction along the direction of the arrow A toward the test piece 12, and since the measuring portion 32 is disposed at the distal end in an opposite direction to the patient, it is less likely for the patient to experience discomfort. Further, since the barcode reader 48 is provided in an opposite direction, operations for measurement of blood glucose and reading of data can easily be distinguished from each other.

Since the barcode reader 48, the test piece 12 and the measuring portion 32 are provided on opposite sides from each other, there is a degree of freedom in design layout, and for example, an intermediate portion 46 can be formed suitably thin. An auxiliary function button, which has a function unique for hospital use, may be provided in place of the data reading button 40.

Next, the shape of the blood glucose meter 10a shall be described. For convenience of description, the display face of the monitor 34 is defined as an upper side, whereas the opposite side is defined as a lower side. However, naturally, orientation of the blood glucose meter 10a during use, during storage and so forth is not limited to such definitions.

The housing of the blood glucose meter 10a is principally configured from an upper housing 42a, on which the monitor 34 and the operation button group 38 are provided, and a lower housing 42b, which is joined to the upper housing 42a and makes up a lower side portion. When the blood glucose meter 10a is placed on a table, at portions of the lower housing 42b, small projections 43 are provided where the lower housing 42b comes into contact with the table T.

The blood glucose meter 10a can be segmented, as viewed from above (refer to FIG. 2), into a main portion 44 on which the monitor 34 and the operation button group 38 are provided, and an intermediate portion 46, which is provided between the main portion 44 and the distal end mounting portion 30. The intermediate portion 46 is configured to have a width that decreases from the main portion 44 continuously and concavely toward the distal end side. The distal end mounting portion 30 is provided on a distal end face of the intermediate portion 46. The data reading button 40 is provided directly at a boundary between the main portion 44 and the intermediate portion 46, so that the data reading button 40 can be touched and operated easily.

The main portion 44 includes the monitor 34 provided thereon and has a certain width, which enables the main portion 44 to be grasped by the hand of a user. The main portion 44 has a substantially fixed width as viewed from above (refer to FIG. 2) in a longitudinal direction (in the direction of the arrow A shown in FIGS. 2 and 3), and has a substantially fixed thickness in a vertical direction as viewed in side elevation (refer to FIG. 3). Consequently, the main portion 44 can be grasped easily. Furthermore, the blood glucose meter 10a is symmetric in shape in leftward and rightward directions, and can be grasped easily by either the right hand or the left hand.

Figure 7:
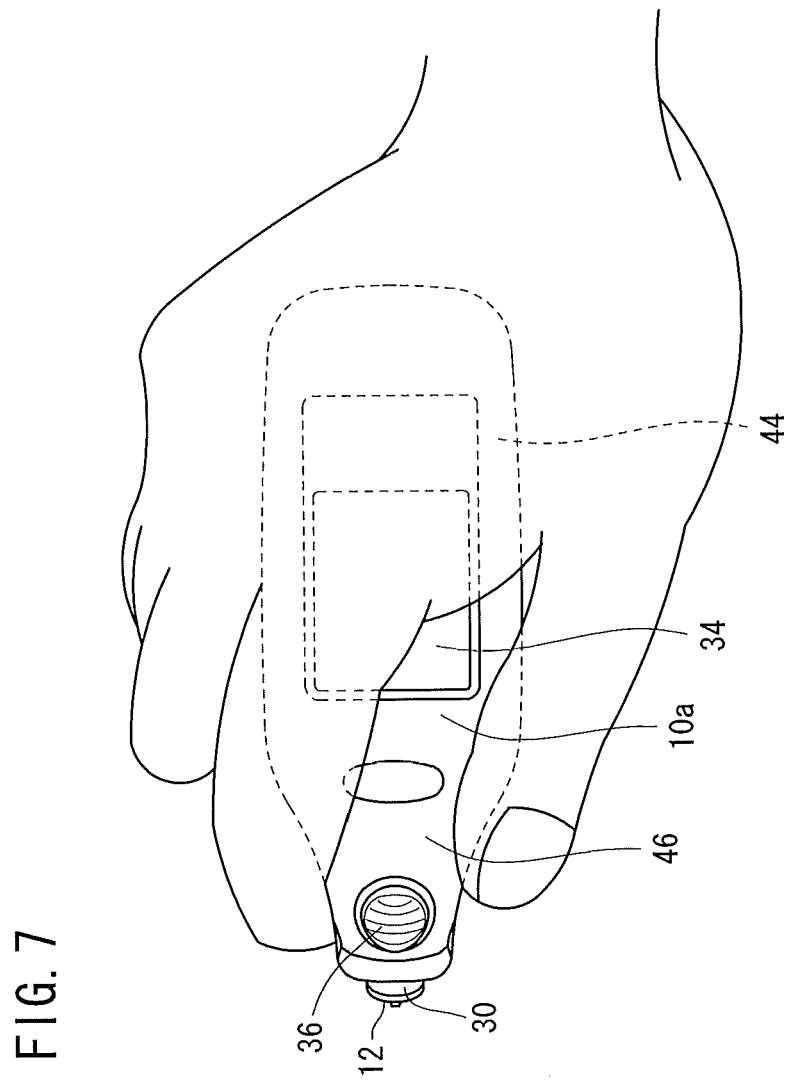
FIG. 7 is a schematic view of the blood glucose meter in a state in which an intermediate portion thereof is grasped.

The blood glucose meter 10a can be grasped not only at the main portion 44 but also at the intermediate portion 46. As shown in FIG. 7, since the intermediate portion 46 has a width that decreases continuously and concavely toward the distal end side from the main portion 44, and since the intermediate portion 46 is suitably thin and concave, the intermediate portion 46 can be grasped easily by the fingertips. Further, since the intermediate portion 46 is positioned near to the distal end mounting portion 30, the mounted test piece 12 can be stabilized by grasping the intermediate portion 46.

On the intermediate portion 46, a space is provided in a suitable direction, in which several mechanisms relating to the distal end mounting portion 30 (for example, the measuring portion 32 for the test paper 20, an ejector mechanism for the test piece 12, a mechanism for holding the distal end mounting portion 30, and so forth) are disposed. Further, as a result of providing the intermediate portion 46, the center axial line C of the test piece 12 can easily be oriented in an obliquely downward direction toward the distal end side. Further, the upper face 46a of the intermediate portion 46 is set substantially parallel to the center axial line C of the test piece 12, and therefore the direction of the test piece 12 can easily be perceived visually.

Further, the ejector lever 36 is provided on the upper face 46a of the intermediate portion 46. Since the ejector lever 36 is moved along the upper face 46a, operation of the ejector lever 36 is facilitated and a space for movement of the ejector lever 36 can be assured.

Assuming that the display face of the monitor 34 defines the upper side, whereas the opposite side to the display face defines the lower side as viewed in side elevation (see FIG. 3), the center axial line C is directed obliquely downward toward the distal end side, with reference to a line of extension L of the display face of the monitor 34. In other words, when the monitor 34 is placed on a horizontal table T (horizontal plane) with the display face of the monitor 34 directed upwardly, the center axial line C of the test piece 12 is directed obliquely downward toward the distal end side. At this time, the angle θ1 defined between the line of extension L and the center axial line C is set at 27°, and the angle θ2 defined between the line of extension L and the table T is set at 7°. Further, the test piece 12, which is mounted on the distal end mounting portion 30, is spaced from the table T, such that no unnecessary external forces are applied to the test piece 12.

A lower face of the main portion 44 and a lower face of the intermediate portion 46 are connected to each other by a continuous curved face portion 50, which is concave as viewed in side elevation. A finger receiving projection 52 is provided at a neighboring portion on the proximal end side, as viewed from the curved face portion 50. The finger receiving projection 52 has a low triangular shape as viewed in side elevation, and forms a smooth arc together with the curved face portion 50, such that a space is formed into which a single finger can be inserted. If the radius of curvature of the curved face portion is 5 mm to 25 mm, and more preferably 8 mm to 20 mm, then a finger can easily be placed thereon in a suitable manner. Since, as described above, it is easy to place a finger on the curved face portion 50, the blood glucose meter 10a can be grasped readily.

Figure 6:
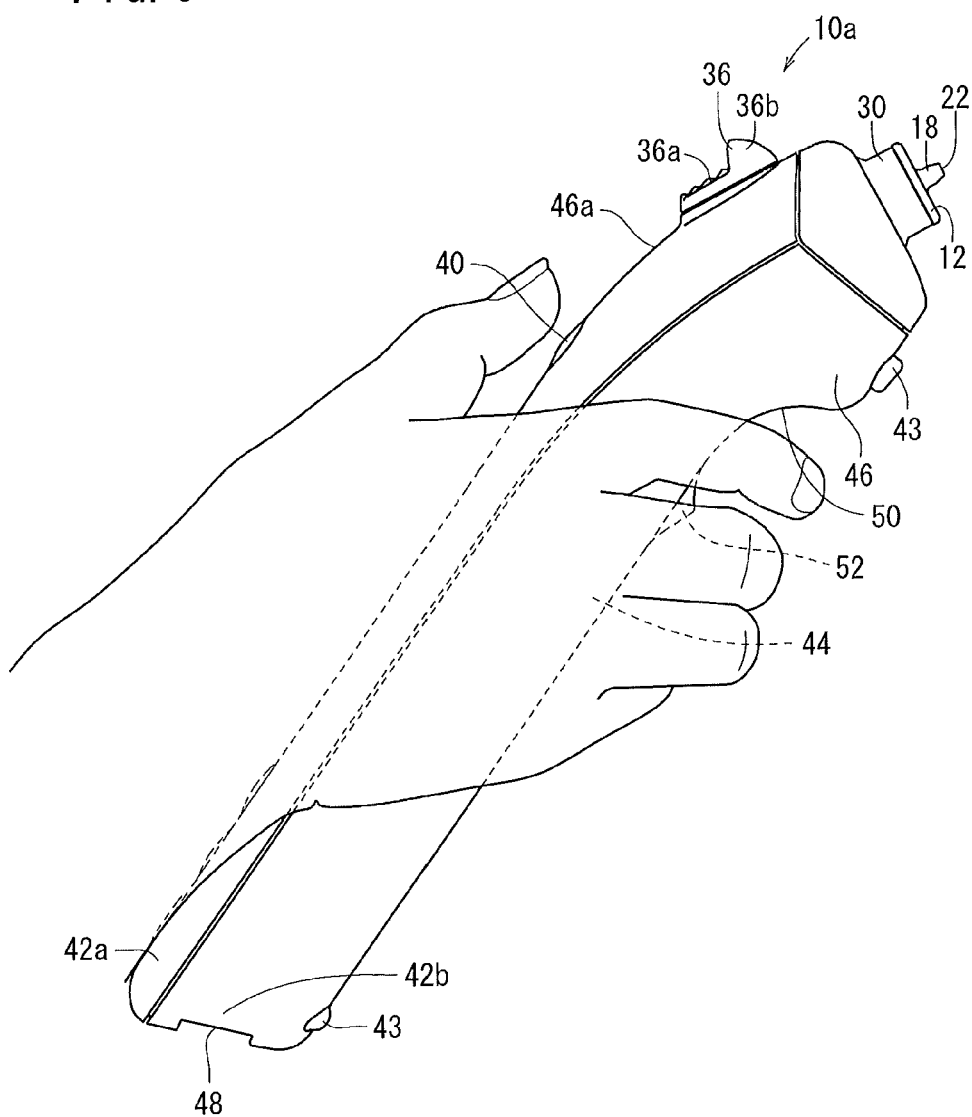
FIG. 6 is a side elevational view of the blood glucose meter in a state of being grasped with a finger placed on a curved face portion.

In particular, as shown in FIG. 6, the blood glucose meter 10a can be grasped stably by placing a finger (for example, the forefinger) on the curved face portion 50. Since the curved face portion 50, the lower face of which is concave, is provided on the connecting portion between the main portion 44 and the intermediate portion 46, the finger is placed on the curved face portion 50 in order to stabilize the blood glucose meter 10a, whereby optical reading by the barcode reader 48 can be carried out stably.

Further, the data reading button 40 is provided on a side substantially opposite to the curved face portion 50, and is held by and between the finger (for example, the forefinger) that is placed on the curved face portion 50 and another finger (for example, the thumb), which presses the data reading button 40, so as to allow stable grasping and operation of the data reading button 40.

The concave curved face portion 50 can be used as a grasping portion. Further, since the concave curved face portion 50 is positioned near the distal end mounting portion 30, it is easy to adjust the position of the spotted portion 22 with respect to a blood drop 60, which makes operations as stable as possible.

The distance H1 between the spotted portion 22 of the blood glucose meter 10a and the table T is 13 mm, and the distance H2 between the highest point P of the lower face and the table T is 11 mm. The highest point P forms a part of the curved face portion 50.

Since the spotted portion 22 is an operation object portion during blood glucose measurement, good visibility when operations are performed is demanded. Also, when the blood glucose meter 10a is placed on the table T, good visibility is required to enable state confirmation. Although it is preferable for the spotted portion 22 to be kept in a spaced relation from the table T, the spotted portion 22 should not be spaced away from the table T needlessly. Further, as hereinafter described (refer to FIGS. 12 and 13), if it is taken into consideration to carry out a spotting operation while the blood glucose meter 10a is kept in place on the table T, there is a suitable range for the distance H1. From such a point of view, it is preferable to set the distance H1 within a range from 3 mm to 30 mm, and more preferably, within a range from 9 mm to 14 mm.

When the blood glucose meter 10a, which is placed on the table T, is grasped, preferably, a suitable gap is provided for placement of a finger between the highest point P and the table T. Preferably, the distance H2 is set within a range from 3 mm to 20 mm, and more preferably, within a range from 7 mm to 12 mm.

Next, a method of using the blood glucose meter 10a, which is configured in the foregoing manner, shall be described.

First, a power supply to the blood glucose meter 10a is made available, and a predetermined barcode, which is indicated on an individualized package for the test piece 12, is read by the barcode reader 48.

Figure 8:
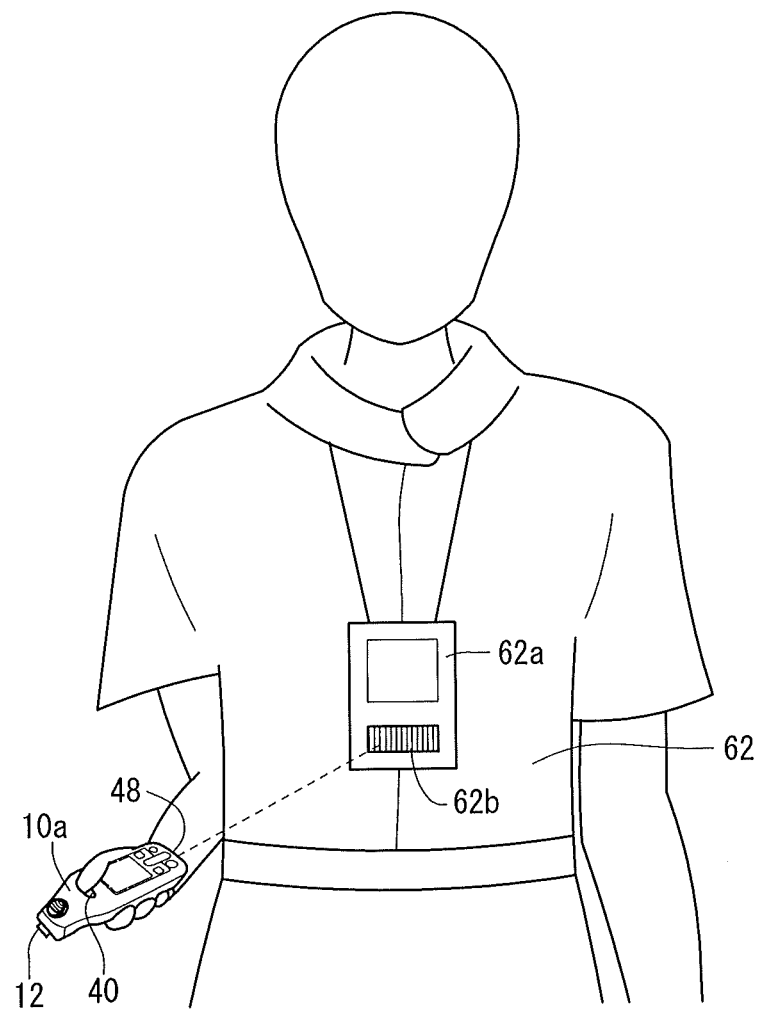
FIG. 8 is a view illustrating a manner in which a health care worker reads measuring person identification data using the blood glucose meter.

Then, as seen in FIG. 8, a health care worker 62 directs the barcode reader 48 toward a card, on which a barcode 62b representative of operator identification data of the health care worker 62 is provided, and depresses the data reading button 40 in order to read the operator identification data. The data is recorded together with a blood glucose measurement value. Such data is used, for example, for confirmation of traceability of the procedure.

At this time, as made clear in FIG. 8, since the barcode reader 48 is directed toward the health care worker 62, the laser beam does not hit upon a patient 64 and the patient 64 does not experience any discomfort.

Further, since the barcode reader 48 is provided on an opposite side to the test piece 12, and the data reading button 40 is provided at a position where the button can be operated readily by the thumb or the like, there is no need to change the grasping position of the hand when measurement of a blood component and reading of data are performed, which is efficient.

Figure 9:
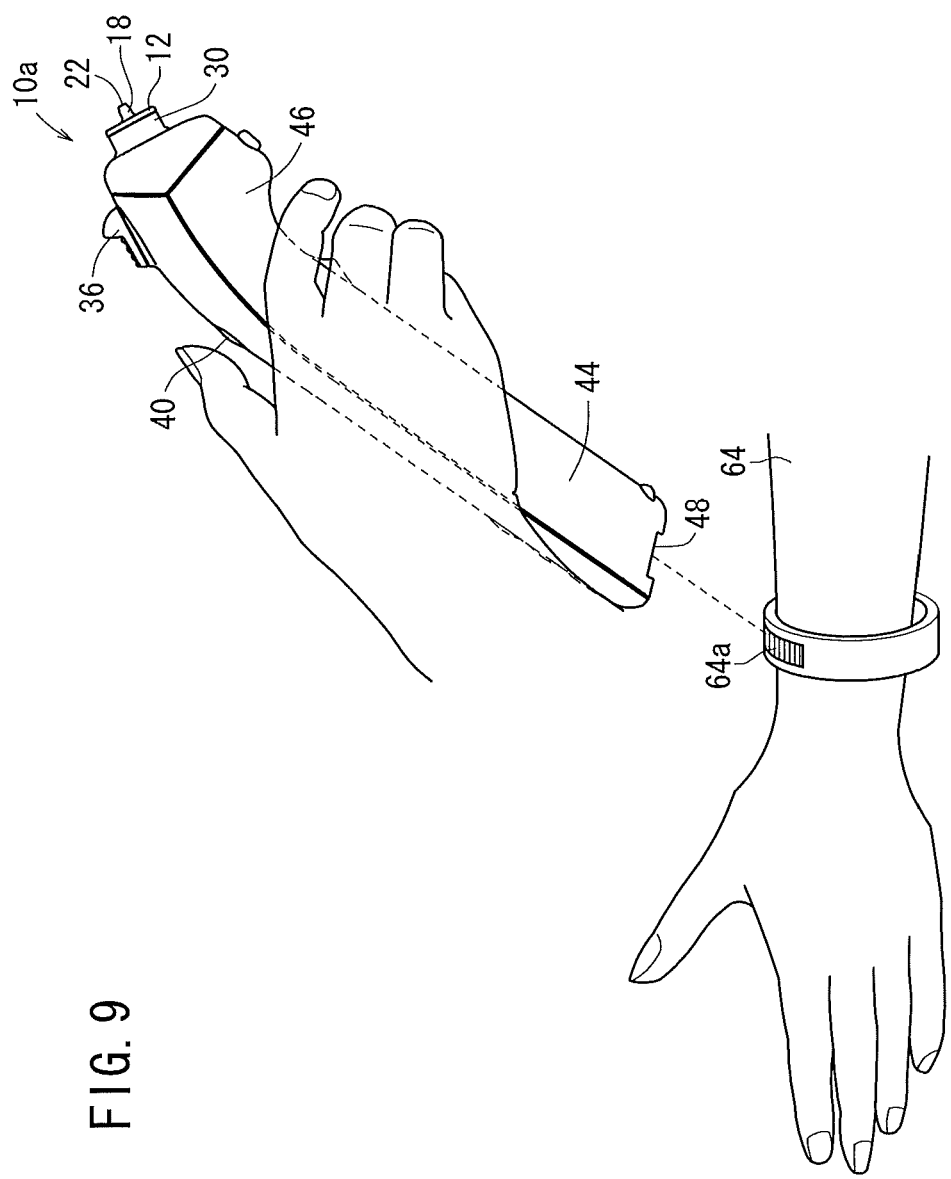
FIG. 9 is a view illustrating a manner in which a health care worker reads patient identification data using the blood glucose meter.

Thereafter, as shown in FIG. 9, patient identification data of the patient 64, which is indicated on a wrist band 64a, is read by the barcode reader 48. Consequently, when a single blood glucose meter 10a is used for taking blood glucose measurements of a plurality of patients, the measured blood glucose levels can be stored distinctively for individual patients.

After the patient identification data, measuring person identification data, and test piece identification data have been read in this manner, the blood glucose meter 10a enters into a measurement mode.

Thereafter, the cap 39 is removed, and the test piece 12 is pushed into the distal end mounting portion 30 together with the individual package casing, until a click is felt. Thereafter, only the casing is removed. By this operation, the test piece 12 becomes mounted on the distal end mounting portion 30. After the test paper 20 has been detected, the measuring portion 32 displays the word "OK" on the monitor 34, and then automatically enters into the blood glucose measurement mode. Further, puncturing is carried out by a predetermined puncturing device in order to provide a blood drop 60 on a fingertip (in the following description, on the forefinger of the left hand).

Figure 10:
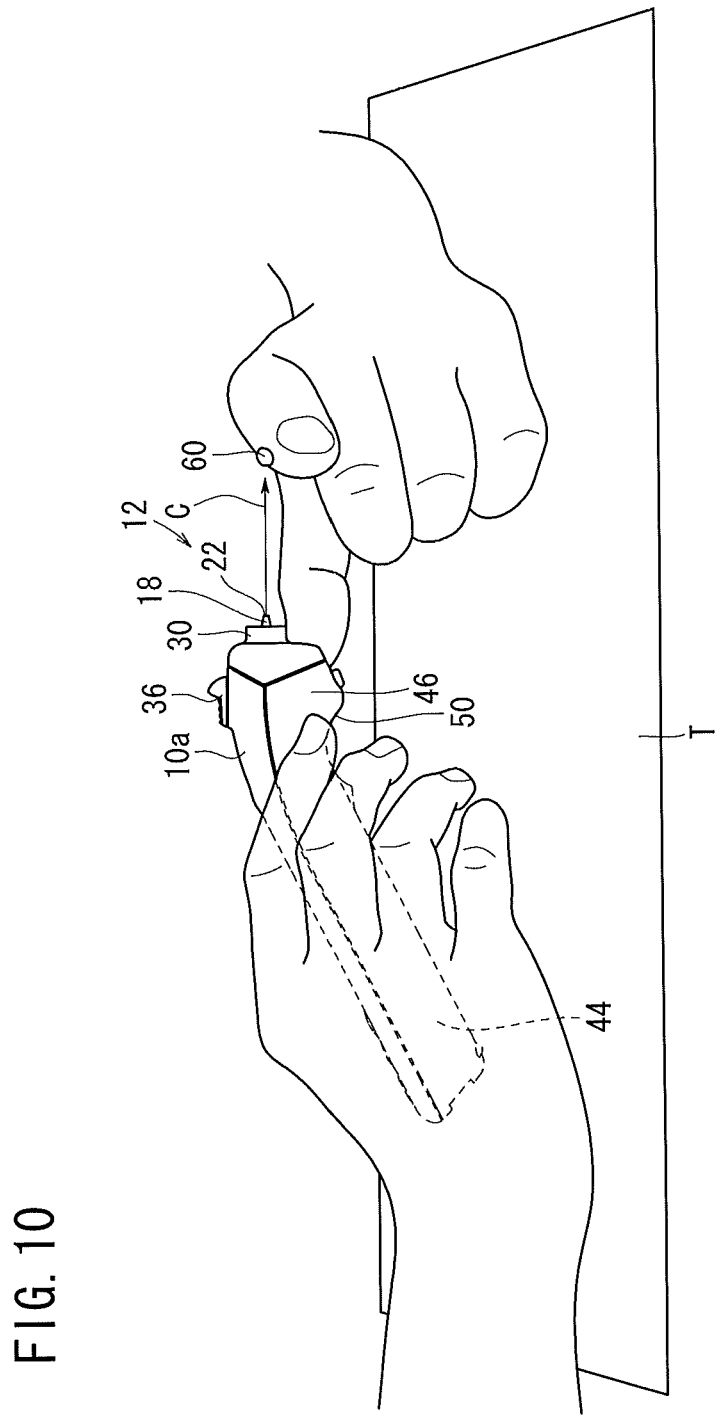
FIG. 10 is a schematic view at a preceding stage before a spotting operation is carried out with the wrists or neighboring portions of the left and right hands being placed on a table, and while the blood glucose meter is grasped.

As shown in FIG. 10, the patient then carries out a spotting action by bringing the spotted portion 22 of the test piece 12 into contact with the blood drop 60, while the patient grasps the blood glucose meter 10a with the right hand. At this time, the left and right wrists or neighboring portions thereof are placed in a stabilized state on the table T.

As is apparent from FIG. 10, if the left and right wrist portions are placed in an ordinary manner on the table T, then backs of the hands are directed obliquely outward while the forefinger of the left hand is directed inwardly, and the main portion 44 of the blood glucose meter 10a, which is grasped by the palm of the right hand, is directed obliquely inward. Consequently, since the intermediate portion 46 is bent at an angle of $\theta 1$ ($=27°$) with respect to the main portion 44, the projection 18 and the center axial line C of the test piece 12 are directed inwardly and extend substantially in a horizontal direction toward the blood drop 60. At this time, the blood drop 60 on the left hand and the spotted portion 22 on the right hand side are directed inwardly and positioned near to each other. In addition, the line of sight of the patient is not interrupted, and consequently, visibility is good.

Figure 11:
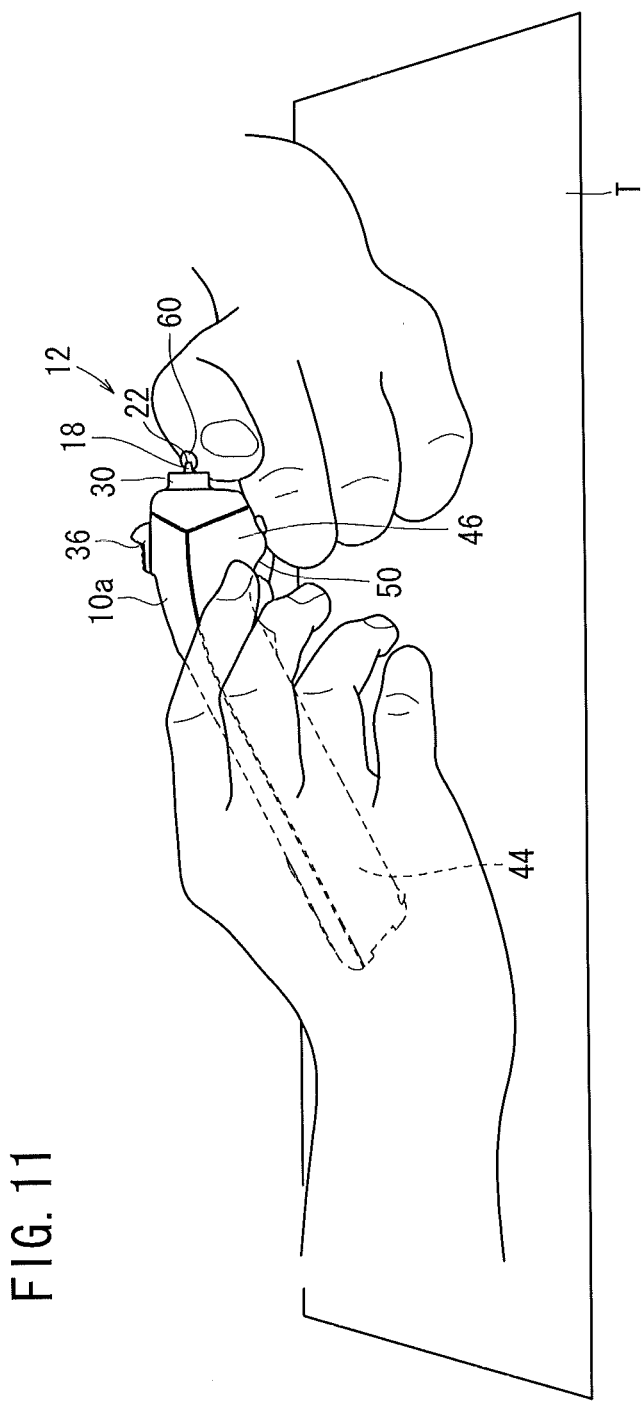
FIG. 11 is a schematic view showing a state in which a spotting operation is carried out with the wrists or neighboring portions of the left and right hands being placed on a table, and while the blood glucose meter is grasped.

Then, the right hand and the left hand are moved toward each other substantially in a horizontal direction in order to carry out the spotting operation, while both wrist portions remain placed on the table T, as shown in FIG. 11.

At this time, it is only necessary to lightly twist both wrist portions inwardly, which is a simple operation that can be carried out stably, in a state in which the wrist portions remain placed on the table T. Accordingly, even in the event that the fingers are impaired, or if the person is unfamiliar with operations of the blood glucose meter 10a, the blood drop 60 and the spotted portion 22, both of which are small, can be brought into contact with each other without any shaking of the fingers. Consequently, a reliable spotting operation can be carried out. Since the projection 18 and the center axial line C are placed in contact with each other in a state in which the projection 18 and the center axial line C are directed toward the blood drop 60, the blood drop 60 can be prevented from coming into contact and sticking to a peripheral portion of the spotted portion 22, a side face of the projection 18, or a portion of the flange 16.

Figure 12:
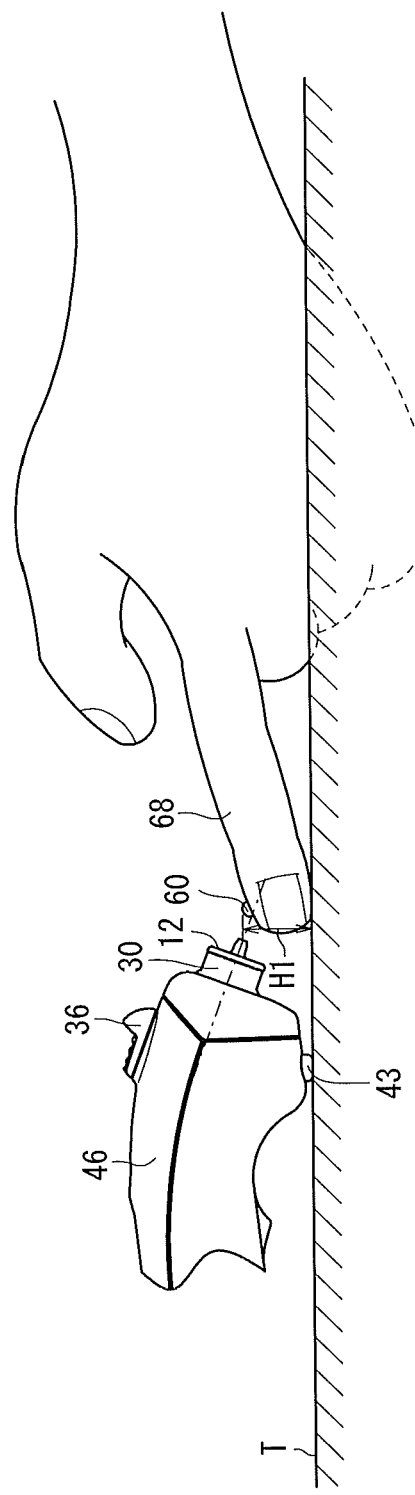
FIG. 12 is a schematic view showing a state in which one finger is placed on a table, and a spotting operation is carried out by the blood glucose meter, which is placed on the table.

As seen in FIG. 12, in order to carry out the spotting operation more reliably, while the blood glucose meter 10a is placed on the table T, the blood glucose meter 10a may be moved closer in order to carry out spotting in a state in which one finger 68 (for example, the forefinger) on which the blood drop 60 is formed remains placed on the table T.

As described above, the distance H1 of the spotted portion 22 from the table T is 13 mm. Meanwhile, if one finger 68 is placed on the table T, then the height of the blood drop 60 is approximately within a range from 3 mm to 20 mm, and ordinarily, is approximately within a range from 5 mm to 14 mm. Thus, even if the height H1 is not initially 13 mm, since the direction and height of the finger 68 can be adjusted within such a range, it is easy to adjust the height with respect to the spotted portion 22, and it is easy to bring the spotted portion 22 into contact with the blood drop 60. At this time, since the finger 68 and the blood glucose meter 10a are placed directly on the table T, the finger 68 and the blood glucose meter 10a are kept highly stable, respectively, so that the spotting operation can be carried out reliably.

Figure 13:
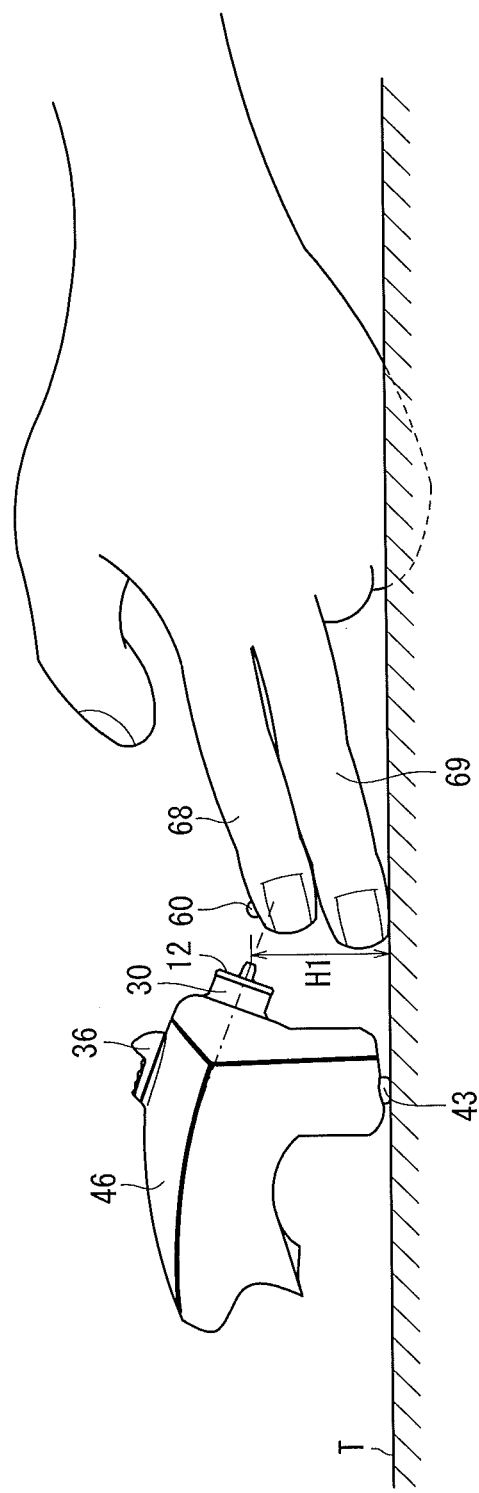
FIG. 13 is a schematic view showing a state in which two fingers are placed on a table, and a spotting operation is carried out by the blood glucose meter, which is placed on the table.

Alternatively, another finger 69 (for example, the middle finger), which is adjacent to the finger 68 on which the blood drop 60 is formed, may be placed on the table T while the finger 68 is placed atop the finger 69, as seen in FIG. 13. If the two fingers 68 and 69 are placed on the table T in this manner, then the height of the blood drop 60 on the upper side finger 68 varies depending on the manner in which the fingers are crossed, the manner of placement of the fingers, and so forth. However, the height as described above generally lies within a range from 5 mm to 30 mm, and ordinarily, lies within a range approximately from 9 mm to 20 mm. Even if the height is not 13 mm initially, since the direction and the height of the finger 68 can be adjusted within such a range, it is easy to adjust the height with respect to the spotted portion 22, and it is easy to bring the spotted portion 22 into contact with the blood drop 60. At this time, since the blood glucose meter 10a is placed directly on the table T, the blood glucose meter 10a is kept highly stable. The finger 68, which is placed on the finger 69, also is kept stable in a suitable manner, whereby a reliable spotting operation can be carried out.

In particular, if the finger 68 alone is placed on the table T (refer to FIG. 12), then stability is high. However, if two fingers, i.e., the finger 68 and the finger 69, are placed on the table T (as shown in FIG. 13), then adjustment of the height of the spotted portion 22 is facilitated. Therefore, either one of the aforementioned spotting operations may be carried out, depending upon the practice and preferences of the patient.

However, if three or more fingers (for example, the forefinger, the middle finger, and the ring finger) are placed on the table T, then even with a healthy person, the finger (forefinger), which is positioned on top of the other fingers, becomes unstable. Moreover, with a patient whose fingers are impaired, the finger that is placed on top sometimes becomes considerably unstable, and it is rather difficult to carry out a spotting operation. Accordingly, it is preferable to set the distance H1 from the table T to the spotted portion 22 to lie within a range from 3 mm to 30 mm, and more preferably, within a range from 9 mm to 14 mm, which represents a height corresponding to one or two fingers.

Naturally, as a method of using the blood glucose meter 10a, in a case where there is no possibility for shaking of the hands or the like to occur, the spotting operation may be carried out in midair, without using the table T.

Consequently, when a correct spotting operation is carried out, the blood drop 60 is sucked into the blood introduction path 24 due to capillary action, whereby the test paper 20 becomes impregnated with blood to a sufficient degree. Thus, the test paper 20 exhibits a color reaction with a reagent in response to the blood glucose level. The measuring portion 32 observes the color reaction of the test paper 20. Then, at a stage in which the color reaction becomes stabilized, based on such a color reaction, the control section 33 performs a predetermined calculation in order to calculate the blood glucose level, and the blood glucose level is displayed on the monitor 34. Further, a notification may be issued by a buzzer in order to indicate that the measurement operation has ended. During observation of the color reaction and during calculation of the blood glucose level, in order to indicate the progress of such observation, a scheduled period of time until measurement is completed may be displayed on the monitor 34.

Thereafter, as a post-processing procedure, in a state where the test piece 12 is covered with the individual package cover, the ejector lever 36 is operated in order to remove the test piece 12 together with the cover. Then, the power supply is turned off, and the cap 39 is placed on the distal end mounting portion 30.

Figure 14:
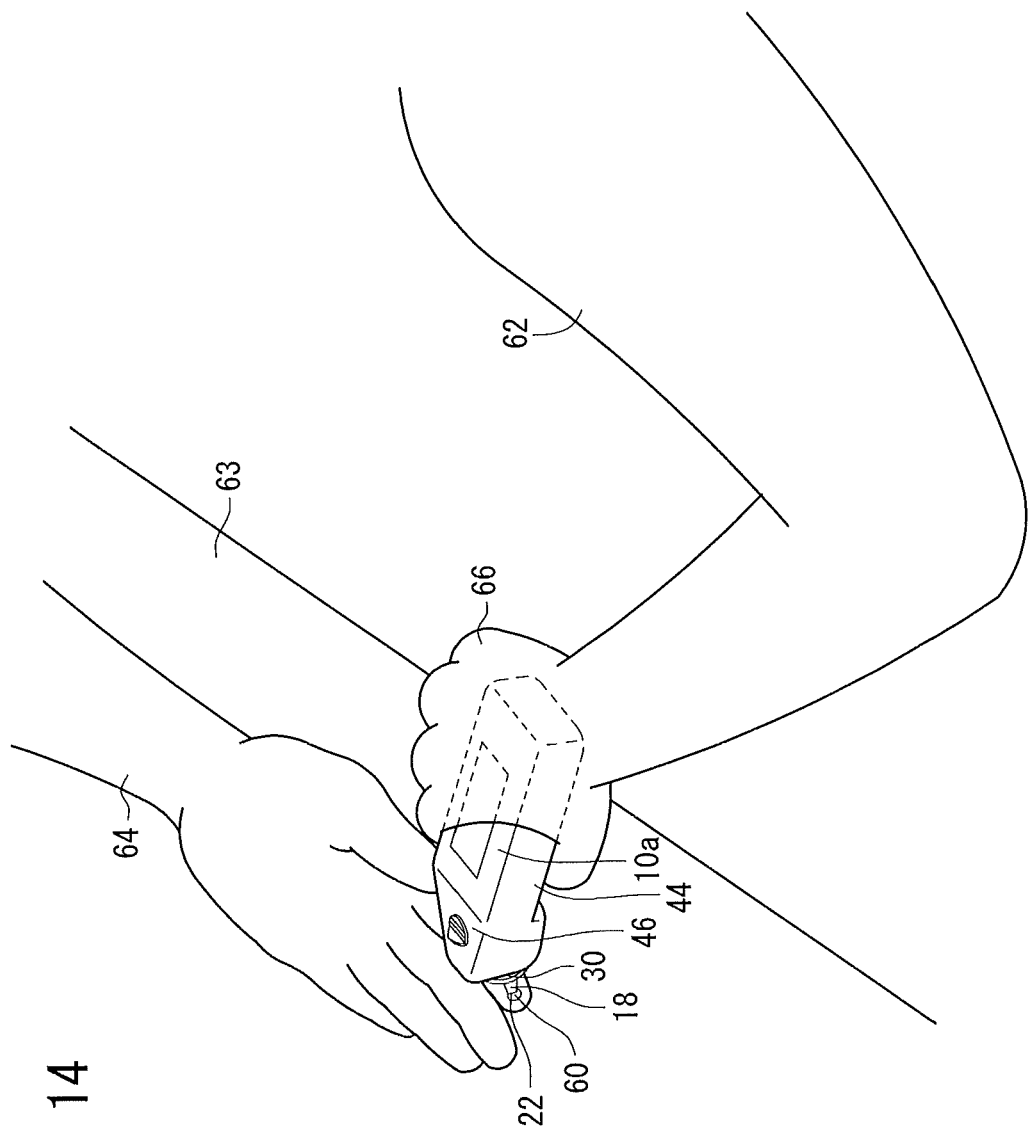
FIG. 14 is a schematic view showing a state in which a health care worker carries out a spotting operation on a patient.
Figure 15:
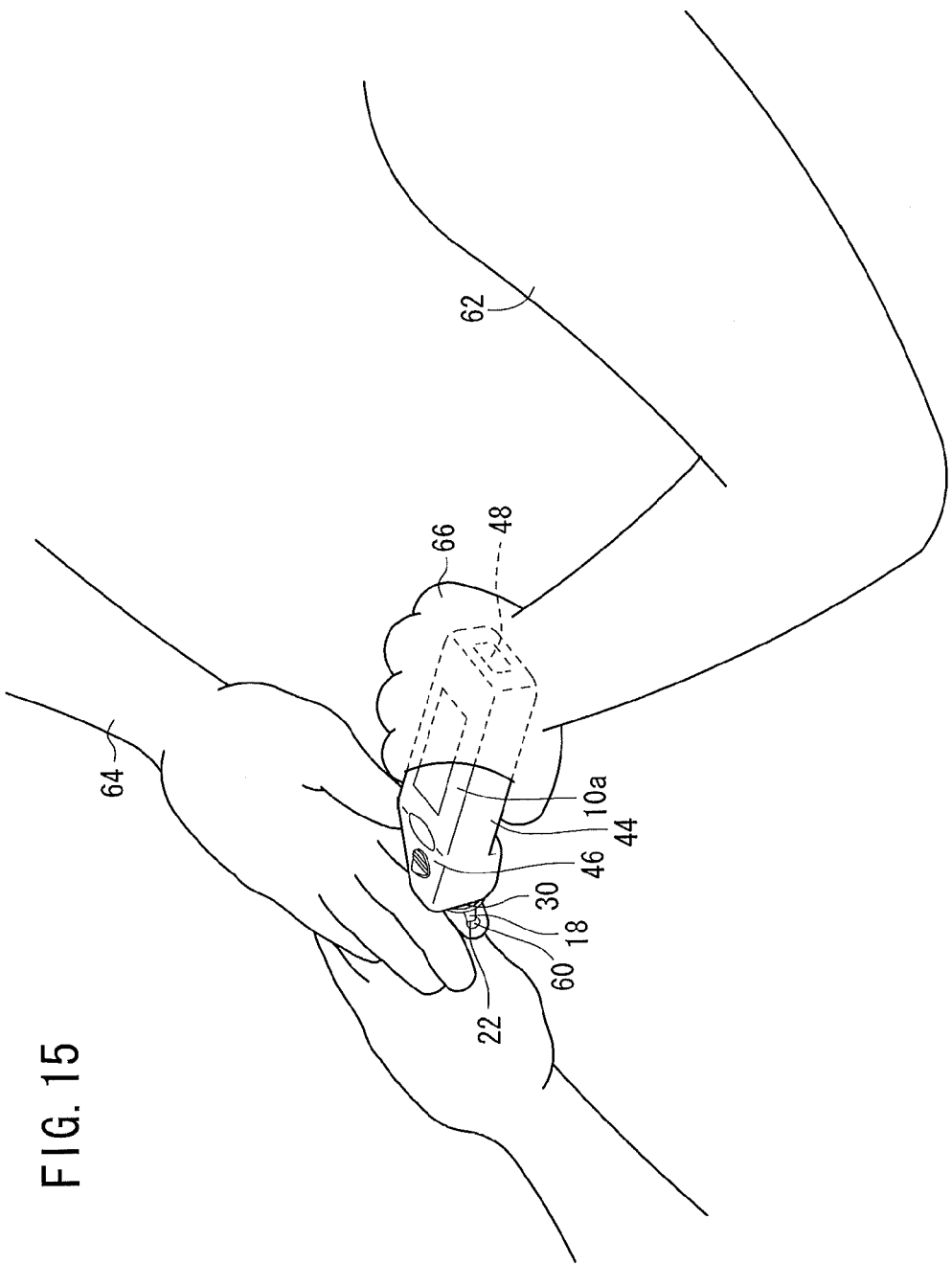
FIG. 15 is a schematic view showing a state in which a health care worker carries out a spotting operation on a patient.

The operation method illustrated in FIGS. 10 to 13 is applied to a case in which the blood glucose meter 10a is intended for personal use, in which a patient carries out blood glucose measurement. Alternatively, a health care worker 62 may carry out operations using the blood glucose meter 10a, as shown in FIGS. 14 and 15. In the case where a health care worker 62 carries out the spotting operation for the patient 64, since the intermediate portion 46 is bent downwardly with respect to the main portion 44, even in a state where the intermediate portion 46 is inclined to some degree, the main portion 44 continues to lie substantially horizontal. Consequently, the health care worker 62 can grasp the blood glucose meter 10a in a comfortable posture with the elbows allowed to suspend downwardly. Further, the palm 66 does not cause a blind spot or otherwise hinder visibility of the blood drop 60 and the spotted portion 22, and visibility is good. Accordingly, when used in a hospital as well, the blood glucose meter 10a allows the spotted portion 22 to be brought into contact with the blood drop 60 easily and reliably so that measurement errors can be suppressed. FIG. 14 illustrates a case in which a health care worker 62 carries out a spotting operation for a patient 64 in a reclining state on a bed 63.

As is apparent from FIG. 15, at this time, even if the data reading button 40 is depressed inadvertently, the laser beam, which is emitted from the barcode reader 48, does not impinge upon the patient 64.

The process illustrated in FIG. 8, the process illustrated in FIG. 9, and the blood glucose measuring process subsequent thereto may be carried out in any order. Among the reading processes of individual identification data, one or more of such processes may be carried out. Alternatively, a configuration in which reading of data is carried out while blood glucose measurement is carried out simultaneously therewith may also be adopted.

As described above, with the blood glucose meter 10a according to the present embodiment, the test piece 12 is provided on the distal end mounting portion 30, and the barcode reader 48 is provided on the opposite rear end face. Therefore, even if the data reading button 40 is depressed inadvertently, a laser beam for scanning is not emitted in a direction toward the patient, and the patient does not experience discomfort. Also, upon reading of patient identification data, although the laser beam may occasionally be oriented in a direction toward the patient, at this time, the user carries out the operation while attention is focused on laser reading, and further, the laser beam merely impinges upon the wrist band 64a and is not directed toward the face of the patient.

Further, the barcode reader 48 and the test piece 12 are sufficiently spaced away from each other, and the measurement directions thereof are opposite to each other. Therefore, when reading by the barcode reader 48 is carried out, a situation in which the test piece 12 comes into contact against some other substance does not occur. In other words, before the blood glucose level is measured, the spotted portion 22 of the test piece 12 does not become soiled or broken, so that correct measurement can be carried out. After a blood glucose level measurement has been performed, although blood sticks to the spotted portion 22, a situation in which the blood sticks to and becomes soiled due to some other substance does not occur.

Further, the monitor 34 is provided on the rear side with respect to the data reading button 40, and the intermediate portion 46 and the distal end mounting portion 30, which are provided on the distal end side with respect thereto, are suitably thin and light and in good balance. Thus, if the intermediate portion 46 or the curved face portion 50 is grasped, then the test piece 12, which is positioned closely thereto, can be stabilized (refer to FIG. 7).

Furthermore, since the blood glucose level measuring operation by the test piece 12, and reading of data by the barcode reader 48 are clearly different from each other, incorrect operations are prevented. By using the barcode reader 48 as an optical data reading means, simple and convenient reading of data can be achieved in a contactless manner. The optical data reading means is oriented suitably, and can carry out reliable reading of data without the possibility of interference, as in wireless communications.

Since the curved face portion 50, the lower face of which is concave, is provided at a location of connection between the main portion 44 and the intermediate portion 46, a finger can be placed thereon in order to stabilize the blood glucose meter 10a, so that optical reading by the barcode reader 48 can be carried out stably.

Data read by the barcode reader 48 may be transferred to a predetermined data management computer through a predetermined communication port, a memory card, or the like. An optical data transmission means (for example, IrDA (Infrared Data Association)) may be provided in accordance with the optical data reading means, such that data of measured blood glucose levels or the like can be transmitted to the management computer.

Further, the blood glucose meter 10a according to the present embodiment is shaped such that, when the blood glucose meter 10a is placed on a horizontal table T, the center axial line C of the test piece 12 is directed obliquely downward toward the distal end side. (In other words, the blood glucose meter 10a is shaped such that the center axial line C is directed obliquely downward toward the distal end side, with reference to a line of extension L of the display face of the monitor 34). Consequently, it is easy to orient the spotted portion 22 of the test piece in a direction toward the blood drop, and the spotted portion 22 of the test piece 12 can be brought into contact with the blood drop 60 obtained by puncture easily and reliably, so that measurement errors can be suppressed.

In order to orient the spotted portion 22 more correctly in a direction toward the blood drop 60, the angle 81 defined between the line of extension L and the center axial line C is set to 10° or greater, and more preferably, to 15° or greater. On the other hand, if the angle θ1 is set to a large value, then since the intermediate portion 46 may be directed downwardly by an excessive amount, there is a possibility, when the blood glucose meter 10a is grasped and the blood glucose meter 10a is positioned, for visibility of the spotted portion 22 to become worse. Further, the feeling of stability may become impaired, or the spotted portion 22 may not be oriented properly in a direction toward the blood drop 60, or when the blood glucose meter 10a is placed in position, the test piece 12 may come into contact with the table T. Accordingly, the angle θ1 is set to 40° or less, and more preferably, to 30° or less. Ultimately, when attention is paid to influence on dimensions of the associated portions, the angle θ1 may be set within a range of 10° to 40°, and more preferably, within a range of 15° to 30°.

Next, blood glucose meters 10b, 10c and 10d according to certain modifications shall be described. Portions of the blood glucose meters 10b to 10d, which are the same as those of the blood glucose meter 10a, are denoted by like reference characters and detailed descriptions of such features shall be omitted.

Figure 16:
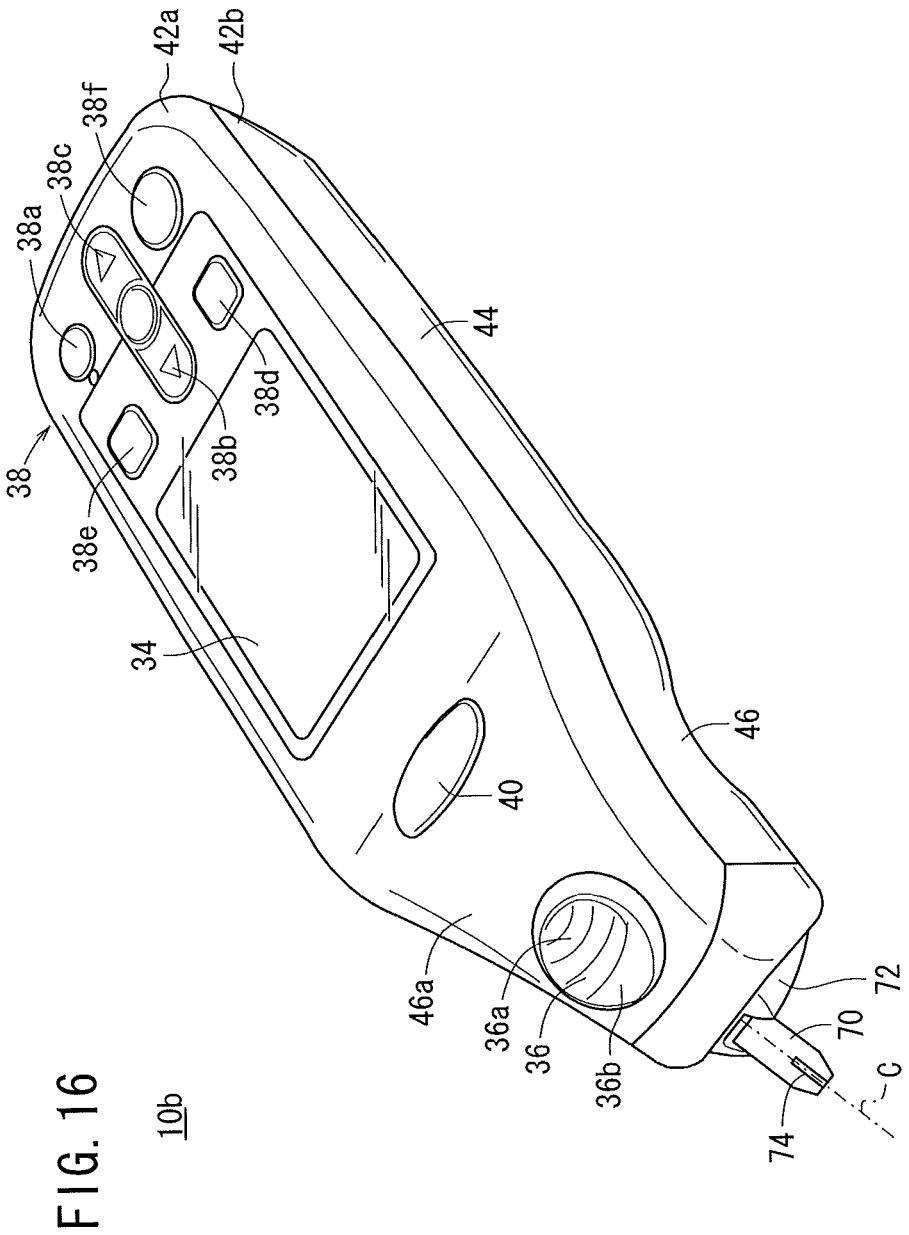
FIG. 16 is a perspective view of a blood glucose meter according to a first modification.
Figure 17:
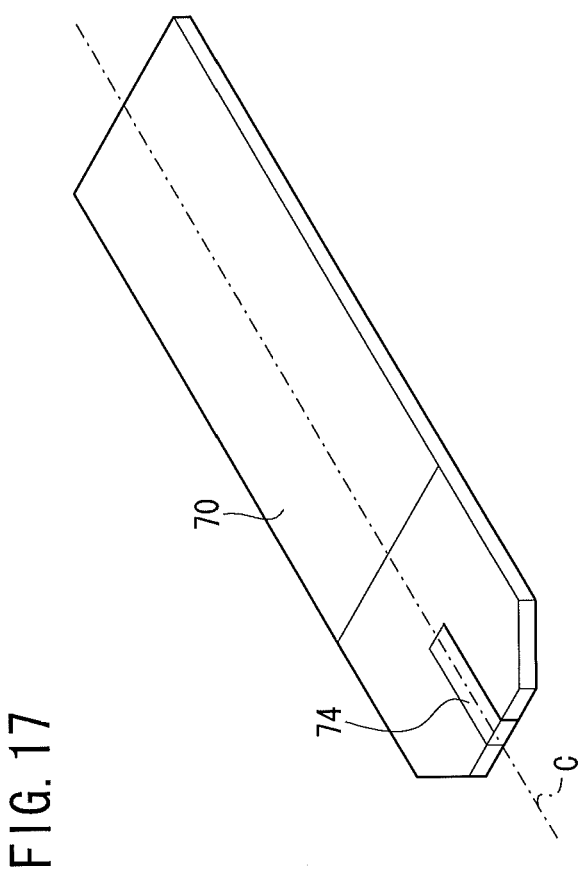
FIG. 17 is a perspective view of a test piece applied to the blood glucose meter according to the first modification.

As shown in FIG. 16, in the blood glucose meter 10b according to the first modification, the distal end mounting portion 30 of the blood glucose meter 10a is replaced by a distal end mounting portion 72 on which a test piece 70 can be mounted. As shown in FIG. 17, the test piece 70 is in the form of a thin narrow plate having a blood introduction path 74 provided on a center axial line C thereof. A conventional article can be used as the test piece 70.

Differently from the blood glucose meter 10a described above, in the blood glucose meter 10b, the measuring portion 32 measures the blood glucose level of sampled blood based on a current value, which is calculated not by an optical means but by an electro-chemical sensor.

In the blood glucose meter 10b, similar to the blood glucose meter 10a described above, the center axial line C of the test piece 70 is directed obliquely downward toward the distal end side, and the angle θ1 defined between the line of extension L and the center axial line C is set to 27°.

Figure 18:
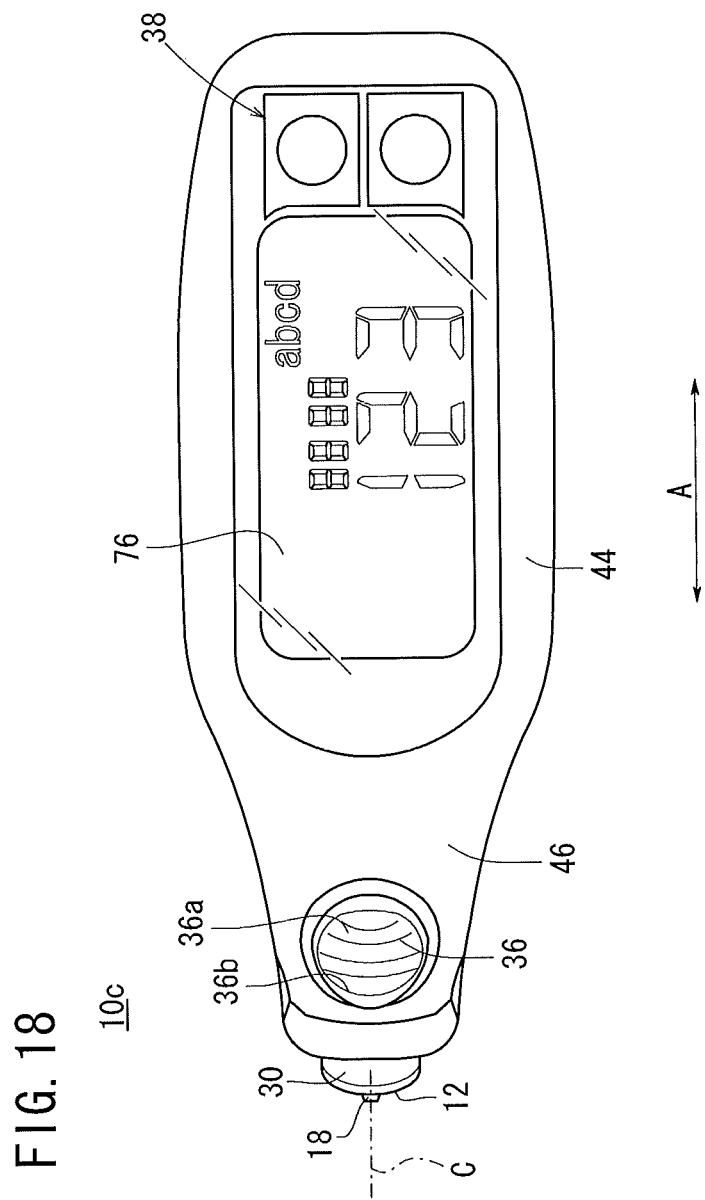
FIG. 18 is a plan view of a blood glucose meter according to a second modification.
Figure 19:
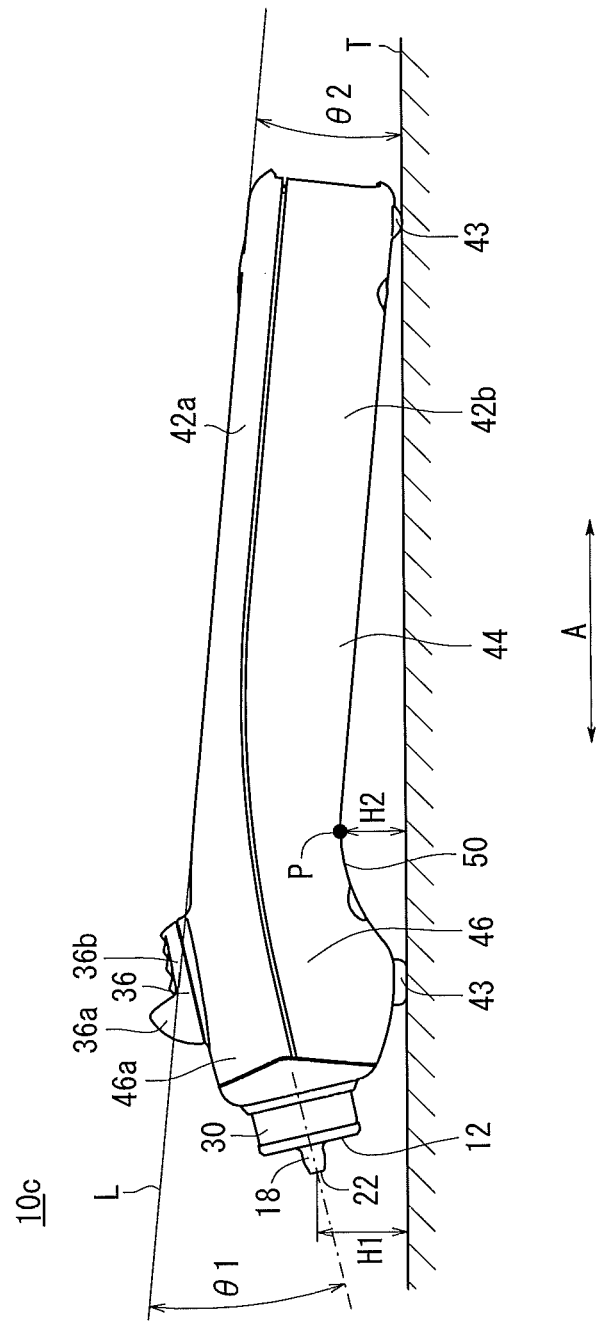
FIG. 19 is a side elevational view of the blood glucose meter according to the second modification.

As shown in FIGS. 18 and 19, the blood glucose meter 10c according to the second modification is configured for personal use, and includes a smaller number of buttons that make up the operation button group 38. The blood glucose meter 10c according to the second modification does not include a data reading button 40 (auxiliary function button), and is smaller in size in comparison with the blood glucose meter 10a. Further, a monitor 76 for displaying blood glucose levels is smaller than the monitor 34 described above.

Since the blood glucose meter 10c is smaller than the blood glucose meter 10a, based on the dimensions of associated portions, the angle θ1 defined between the line of extension L and the center axial line C is set at 18°, the angle θ2 is set at 5°, H1 is set at 10 mm, and H2 is set at 7 mm.

Figure 20:
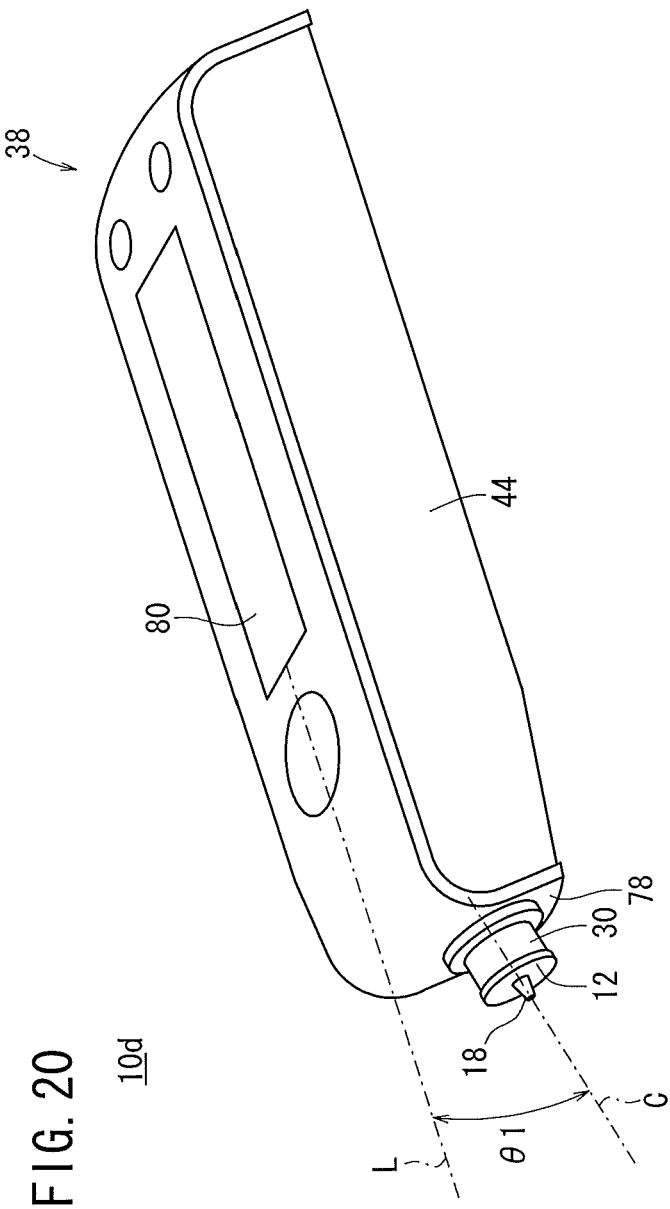
FIG. 20 is a perspective view of a blood glucose meter according to a third modification.
Figure 21:
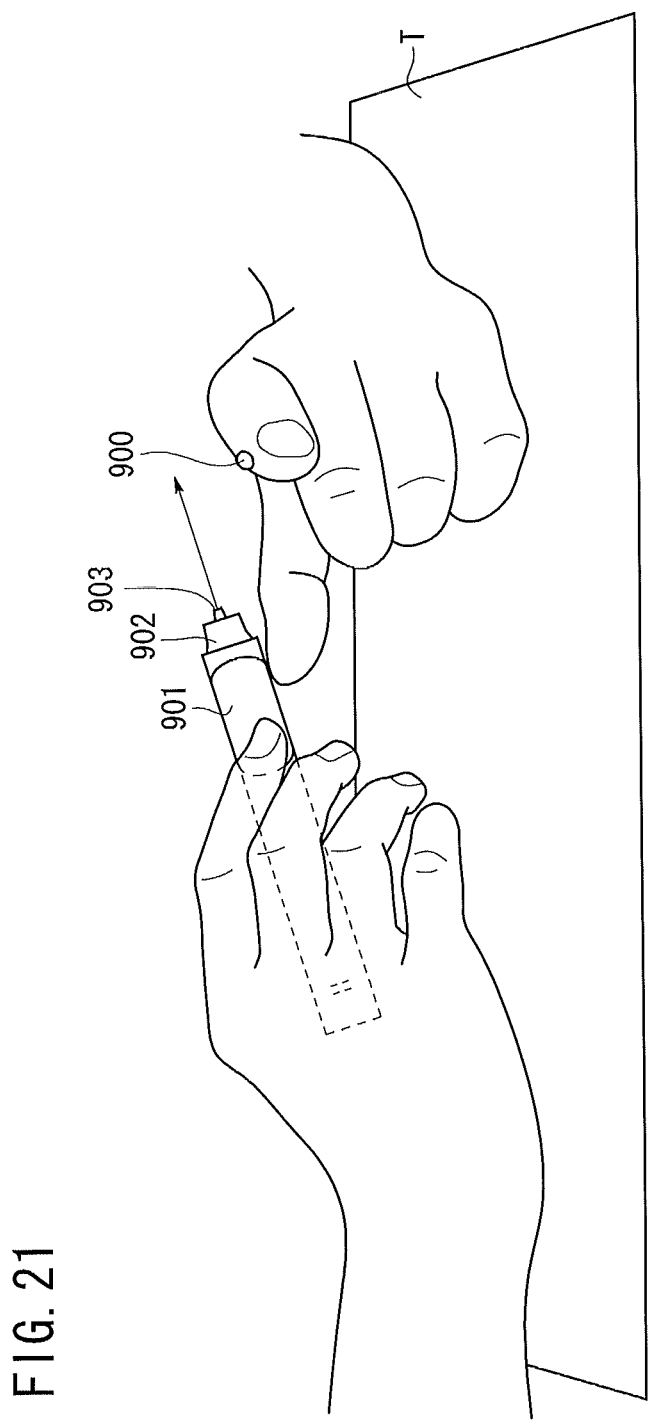
FIG. 21 is a schematic view of a first example in which a spotting operation is carried out by a blood glucose meter according to the conventional art.
Figure 22:
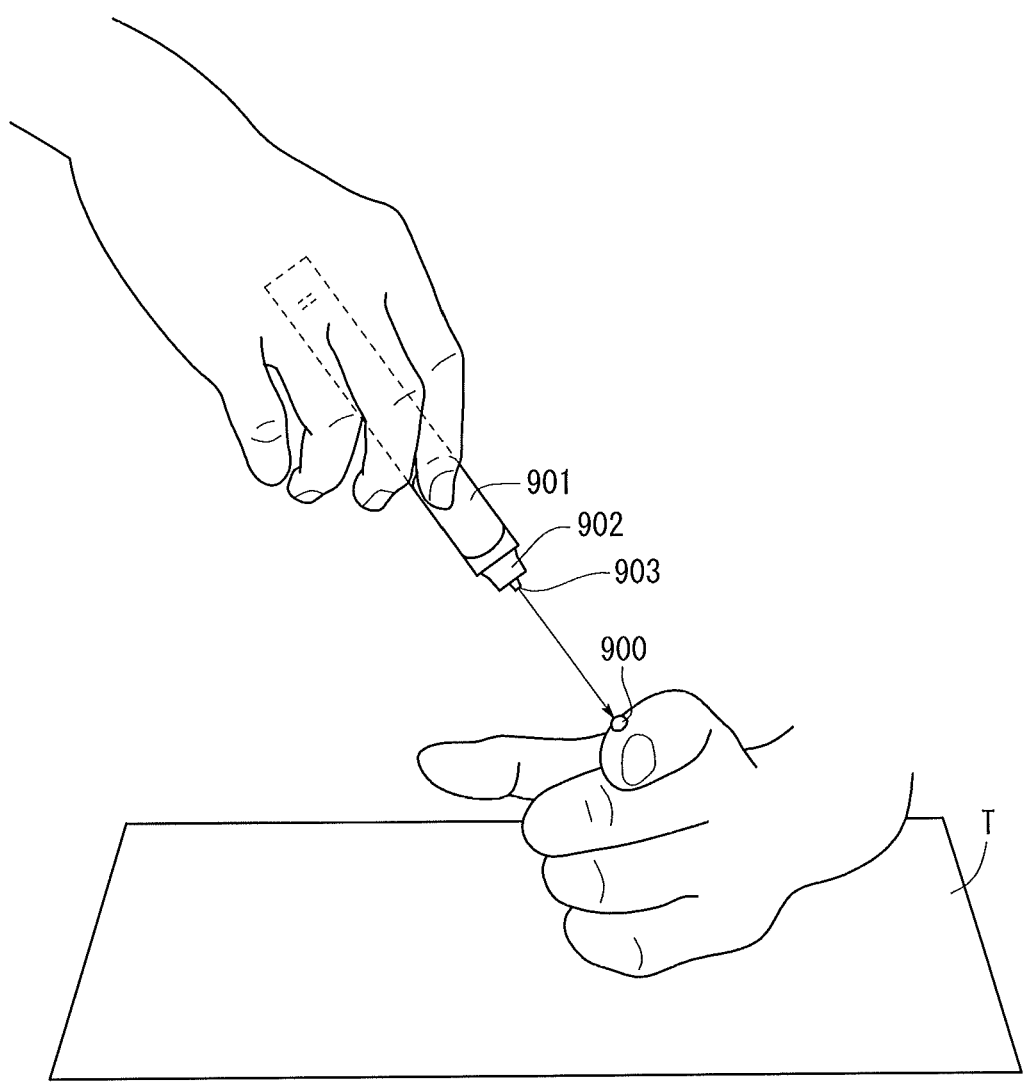
FIG. 22 is a schematic view of a second example in which a spotting operation is carried out by a blood glucose meter according to the conventional art.

As shown in FIG. 20, the blood glucose meter 10d according to the third modification has a small and thin profile, which facilitates carrying thereof, and the blood glucose meter 10d does not include a portion corresponding to the intermediate portion 46 described above, but rather includes a distal end mounting portion 30, which is provided at a distal end portion end face 78 thereof. The distal end portion end face 78 has a shape, which is inclined obliquely as viewed in side elevation (the side elevational view is omitted), and the center axial line C of the test piece 12 is directed obliquely downward toward the distal end side, with reference to the line of extension L of the display face of the monitor 80.

In the blood glucose meters 10b to 10d according to the first to third modifications described above, the center axial line C of the test piece 12 (or the test piece 70) is directed obliquely downward toward the distal end side with reference to the line of extension L, similar to the blood glucose meter 10a described above. Accordingly, in both blood glucose meters for hospital use as well as for personal use, it is easy to direct the spotted portion 22 of the test piece 12 (or the test piece 70) toward the blood drop 60, and the spotted portion 22 can be brought into contact readily and reliably with the blood drop 60 obtained by puncture. Consequently, errors in measurement can be suppressed.

Although the blood glucose meters 10a to 10d measure blood glucose levels as a property of a sample, the present invention is not limited to this example, but can also be applied as an apparatus (blood component measuring apparatus) for measuring hormone levels, cholesterol concentrations, or the like.

The barcode reader 48 in the blood glucose meters 10a and 10b may comprise another type of optical data reading means, which may be, for example, any of a manual scan type, a CCD scan type, a laser scan type, an image sensing type, or the like.

With a scan type apparatus made up of a CCD camera, reading of a two-dimensional code is possible, whereby the amount of information that can be read increases. In the case that a two-dimensional code is read, for example, predetermined prescription information or the like may be read and verified together with a measured blood glucose level in order to determine an insulin dose. However, the type of data to be read by the barcode reader 48 is not limited to the aforementioned example.

The blood component measuring apparatus according to the present invention is not limited to the embodiment described above, but naturally various other configurations could be adopted without departing from the subject matter of the present invention.

The invention claimed is:

1. A blood component measuring apparatus on which a test piece is mountable, comprising:
a distal end mounting portion configured to have mounted thereon the test piece;
a measuring portion adapted to measure components of blood sampled through a blood introduction path provided in the test piece when the test piece is mounted on the distal end mounting portion; and
a monitor adapted to display a result determined by the measuring portion and a predetermined control section,
wherein a display face of the monitor is defined as an upper side, while an opposite face to the display face is defined as a lower side,
the lower side includes at least two surface contacting portions, the two surface contacting portions being spaced apart from one another so that one of the surface contacting portions is positioned distally of another of the surface contacting portions;
wherein, when the test piece is mounted on the distal end mounting portion and the blood component measuring apparatus is placed on a horizontal surface lying in a horizontal plane in a state in which the display face of the monitor is directed upwardly and the two surface contacting portions are in contact with the horizontal surface, a center axial line of the test piece is directed obliquely downward toward a distal end side, and
wherein when the test piece is mounted on the distal end mounting portion and the blood component measuring apparatus is placed on the horizontal surface lying in the horizontal plane in a state in which the display face of the monitor is directed upwardly and the two surface contacting portions are in contact with the horizontal surface, a distance between a spotted portion at the distal end of the test piece and the horizontal plane is 9 mm to 14 mm.

2. The blood component measuring apparatus according to claim 1, further comprising:
a main portion on which the monitor is provided; and
an intermediate portion provided between the main portion and the distal end mounting portion,
wherein an upper face of the intermediate portion is set substantially parallel to the center axial line.

3. The blood component measuring apparatus according to claim 2, wherein
an ejector lever for removing the mounted test piece by performing a push out operation toward the distal end side is provided on the upper face of the intermediate portion.

4. The blood component measuring apparatus according to claim 2, wherein
as viewed from above, the intermediate portion has a width that decreases continuously and concavely from the main portion toward the distal end side.

5. The blood component measuring apparatus according to claim 2, wherein
a thickness of the main portion in a vertical direction is substantially fixed; and
as viewed in side elevation, the main portion and the intermediate portion are connected to each other by a continuously curved face portion, the lower face of which has a concave shape.

6. The blood component measuring apparatus according to claim 1, wherein
when the blood component measuring apparatus is placed on the horizontal plane in a state in which the display face of the monitor is directed upwardly, the distance between a highest point of the lower face and the horizontal plane is 3 mm to 20 mm.

7. The blood component measuring apparatus according to claim 1, wherein
when the test piece is mounted on the distal end mounting portion and the blood component measuring apparatus is placed on the horizontal plane in a state in which the display face of the monitor is directed upwardly, the test piece is spaced from the horizontal plane.

8. A blood component measuring apparatus on which a test piece is mountable, the test piece including a flange, a test paper secured to a surface of the flange and a blood introduction path possessing a distal end opening to a distal end face of the test piece and another end opening to the surface of the flange, the blood introduction path possessing a center axis passing through the test paper, the blood component measuring apparatus comprising:
a distal end mounting portion configured to have mounted thereon the test piece;
a measuring portion adapted to measure components of blood sampled through the blood introduction path provided in the test piece when the test piece is mounted on the distal end mounting portion; and
a monitor adapted to display a result determined by the measuring portion and a predetermined control section,
wherein a display face of the monitor is defined as an upper side, while an opposite face to the display face is defined as a lower side,
wherein the lower side includes at least two projections spaced apart from one another so that one of the projections is positioned closer to the distal end mounting portion that another of the projections;
wherein when the test piece is mounted on the distal end mounting portion and the blood component measuring apparatus is placed on a horizontal surface lying in a horizontal plane such that the two projections are in contact with the horizontal surface, the center axis of the blood introduction path is directed, as viewed in side elevation, obliquely downward toward a distal end side with reference to a line of extension of the display face of the monitor, and
wherein when the test piece is mounted on the distal end mounting portion and the blood component measuring apparatus is placed on the horizontal surface lying in the horizontal plane such that the two projections are in contact with the horizontal surface while the display face of the monitor is directed upwardly, a distance between the distal end of the blood introduction path and the horizontal plane is 9 mm to 14 mm.

9. The blood component measuring apparatus according to claim 8, wherein
an angle defined by the line of extension and the center axial line is 10° to 40°.

10. The blood component measuring apparatus according to claim 8, further comprising:
a main portion on which the monitor is provided; and
an intermediate portion provided between the main portion and the distal end mounting portion,
wherein an upper face of the intermediate portion is set substantially parallel to the center axial line.

11. The blood component measuring apparatus according to claim 10, wherein
an ejector lever for removing the mounted test piece by performing a push out operation toward the distal end side is provided on the upper face of the intermediate portion.

12. The blood component measuring apparatus according to claim 10, wherein
as viewed from above, the intermediate portion has a width that decreases continuously and concavely from the main portion toward the distal end side.

13. The blood component measuring apparatus according to claim 10, wherein
a thickness of the main portion in a vertical direction is substantially fixed; and
as viewed in side elevation, the main portion and the intermediate portion are connected to each other by a continuously curved face portion, the lower face of which has a concave shape.

14. The blood component measuring apparatus according to claim 8, wherein
when the blood component measuring apparatus is placed on a horizontal plane in a state in which the display face of the monitor is directed upwardly, the distance between a highest point of the lower face and the horizontal plane is 3 mm to 20 mm.

15. The blood component measuring apparatus according to claim 8, wherein
when the test piece is mounted on the distal end mounting portion and the blood component measuring apparatus is placed on a horizontal plane in a state in which the display face of the monitor is directed upwardly, the test piece is spaced from the horizontal plane.

16. A test piece in combination with a blood component measuring apparatus positionable on a horizontal surface lying in a horizontal plane,
the test piece comprising a flange, a test paper fixed to a surface of the flange, a projection projecting from the flange in a direction away from the test paper, and a blood introduction path passing through the projection so that a distal end of the blood introduction path opens to a distal end face of the test piece and an opposite end opens to the surface of the flange, the blood introduction path possessing a center axis;
the blood component measuring apparatus comprising:
a distal end mounting portion positioned at a distal end of the apparatus, the test piece being configured to be mounted on the distal end mounting portion;
a measuring portion adapted to measure components of blood sampled through the blood introduction path;
a monitor adapted to display a result determined by the measuring portion and a predetermined control section;
wherein a display face of the monitor is defined as an upper side, while an opposite face to the display face is defined as a lower side;
wherein the lower side is configured to contact the horizontal surface at least at two spaced apart locations when the blood component measuring apparatus is placed on the horizontal surface;
the distal end mounting portion and the test piece being configured and arranged so that when the blood component measuring apparatus is placed on the horizontal surface in a state in which the test piece is mounted on the distal end mounting portion, the blood component measuring apparatus contacts the horizontal surface at the two spaced apart locations and the display face of the monitor is directed upwardly, the center axis of the blood introduction path is oriented obliquely downward toward a distal end side; and
the distal end mounting portion and the test piece also being configured and arranged so that when the test piece is mounted on the distal end mounting portion and the blood component measuring apparatus is placed on the horizontal surface in the state in which the display face of the monitor is directed upwardly and the blood component measuring apparatus contacts the horizontal surface at the two spaced apart locations, a distance between the distal end of the blood introduction path and the horizontal surface is 9 mm to 14 mm.

17. The blood component measuring apparatus according to claim 16, wherein the blood component measuring apparatus comprises a housing and two projections projecting from the housing, the two projections contacting the horizontal surface at the two spaced apart locations when the blood component measuring apparatus is placed on the horizontal surface.

* * * * *